(12) United States Patent
Saliba

(10) Patent No.: US 12,164,067 B2
(45) Date of Patent: *Dec. 10, 2024

(54) LOW-TEMPERATURE PEROVSKITE SCINTILLATORS AND DEVICES WITH LOW-TEMPERATURE PEROVSKITE SCINTILLATORS

(71) Applicant: Michael Saliba, Darmstadt (DE)

(72) Inventor: Michael Saliba, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/473,509

(22) Filed: Sep. 25, 2023

(65) Prior Publication Data

US 2024/0168182 A1   May 23, 2024

Related U.S. Application Data

(63) Continuation of application No. 17/688,584, filed on Mar. 7, 2022, now abandoned, which is a
(Continued)

(51) Int. Cl.
*G01N 23/083* (2018.01)
*A61B 6/00* (2006.01)
(Continued)

(52) U.S. Cl.
CPC .......... *G01T 1/2023* (2013.01); *A61B 6/037* (2013.01); *A61B 6/4208* (2013.01);
(Continued)

(58) Field of Classification Search
None
See application file for complete search history.

(56) References Cited

U.S. PATENT DOCUMENTS 5,961,714 A    10/1999 Melcher
11,269,090 B2*  3/2022 Saliba ...................... G01T 7/00
(Continued)

FOREIGN PATENT DOCUMENTS

EP    1413897 A1    4/2004
JP    2003149345 A  5/2003
(Continued)

OTHER PUBLICATIONS

Kanemiitsu, Yohoshiko, "Luminescence Spectroscopy of Lead-halide Perovskites: Materials Properties and Application as Photovoltaic Devices", 2017, J. Mater. Chem. C., vol. 5, 3427-3437.
(Continued)

*Primary Examiner* — David P Porta
*Assistant Examiner* — Mamadou Faye
(74) *Attorney, Agent, or Firm* — PCFB, LLC; Justin K. Flanagan

(57) ABSTRACT

Disclosed embodiments include perovskite scintillators configured to be operated at a low temperature, detectors with perovskite scintillators configured to be operated at a low temperature, scanners with perovskite scintillators configured to be operated at a low temperature, methods of cooling a perovskite scintillator to a low temperature, and methods of configuring a perovskite scintillator to be operated at a low temperature.

22 Claims, 17 Drawing Sheets

Related U.S. Application Data continuation of application No. 16/843,699, filed on Apr. 8, 2020, now Pat. No. 11,269,090.

(60) Provisional application No. 62/831,992, filed on Apr. 10, 2019.

(51) Int. Cl.
    A61B 6/03    (2006.01)
    A61B 6/42    (2024.01)
    G01N 23/046    (2018.01)
    G01T 1/20    (2006.01)
    G01T 1/202    (2006.01)
    G01T 7/00    (2006.01)

(52) U.S. Cl.
CPC ............ *A61B 6/4488* (2013.01); *A61B 6/481* (2013.01); *G01N 23/046* (2013.01); *G01N 23/083* (2013.01); *G01T 1/2018* (2013.01); *G01T 7/00* (2013.01); *G01N 2223/04* (2013.01); *G01N 2223/419* (2013.01); *G01N 2223/505* (2013.01)

(56) References Cited

U.S. PATENT DOCUMENTS

| | | |
|---|---|---|
| 2004/0129886 A1 | 7/2004 | Lecoq |
| 2004/0173752 A1 | 9/2004 | Shibuya et al. |
| 2018/0136344 A1 | 5/2018 | Nelson |
| 2018/0321393 A1 | 11/2018 | Wu |
| 2020/0209414 A1 | 7/2020 | Birowosuto |

FOREIGN PATENT DOCUMENTS

| | | |
|---|---|---|
| JP | 2004532997 A | 10/2004 |
| WO | 2018021975 A1 | 2/2018 |
| WO | 20200208606 A1 | 10/2020 |

OTHER PUBLICATIONS

Ahmed et al., "Characterisation of Tungstate and Molybdate Crystals ABO4 (A=Ca, Sr,Zn, Cd; B=W, Mo), for Luminescence Lifetime Cryothermometry", 2018, Materialia vol. 4, pp. 287-296.

Birowosuto et al., "High-light-output Scintillator for Photodiode Readout: LuI3:Ce3 ", Jun. 2006, Journal of Applied Physics, vol. 99, pp. 1-4.

Birowosuto et al., "X-ray Scintillation in Lead Halide Perovskite Crystals", Nov. 16, 2016, Nature: Scientific Reports, vol. 6, pp. 1-10.

Bizarri et al., "Scintillation Properties of O 1 X! Inch3 LaBr3 5%Ce3 Crystal", Apr. 2006, IEEE Transactions on Nuclear Science, vol. 53, No. 2, pp. 615-619.

Blahuta et al., "Evidence and Consequences of Ce4 in LYSO:Ce, Ca and LYSO:Ce,Mg Single Crystals for Medical Imaging Applications", Aug. 2013, IEEE Transactions on Nuclear Science, vol. 60, No. 4, pp. 3134-3141.

Bondar et al., "MPPC versus MRS APO in two-phase Cryogenic Avalanche Detectors", Apr. 27, 2015, Journal of Instrumentation, vol. 10, pp. 1-11.

Cates et al., "Advances in Coincidence Time Resolution for PET", 2016, Phys. Med. Biol., vol. 61, pp. 2255-2264.

Chen et al., "All-inorganic Perovskite Nanocrystal Scintillators," Sep. 6, 2018, Nature, vol. 561, pp. 88-93.

Chen et al., "Composition-Dependent Energy Splitting between Bright and Dark Excitons in Lead Halide Perovskite Nanocrystals", Feb. 21, 2018, Nano Lett., vol. 18, pp. 2074-2080.

Dar et al., "Origin of Unusual Bandgap Shift and Dual Emission in Organic-inorganic Lead Halide Perovskites", Oct. 28, 2016, Sci. Adv., vol. 2, pp. 1-9.

De Haas et al., "Advances in Yield Calibration of Scintillators", Jun. 2008, IEEE Transactions on Nuclear Science, vol. 55, No. 3, pp. 1086-1092.

Derenzo et al., "Bright and Ultra-fast Scintillation from a Semiconductor?", Jan. 1, 2016, Nucl. Instrum. Methods. Phys. Res., vol. 805, pp. 1-10.

Derenzo et al., "Design and Implementation of a Facility for Discovery New Scintillator Materials", Jul. 2008, IEEE Trans. Nucl. Sci., pp. 1-7.

Derenzo et al., "Fundamental Limits of Scintillation Detector Timing Precision", Jul. 7, 2014, Phys. Med. Biol., vol. 59, No. 13, pp. 3261-3286.

Derenzo et al., "Temperature Dependence of the Fast, Near-band-edge Scintillation from CUI, Hg 12, PbI2, ZnO: Ga and CdS:In", 2002, Nuclear Instruments and Methods in Physics Research A, vol. 486, pp. 215-219.

Diab et al., "Narrow Linewidth Excitonic Emission in Organic-Inorganic Lead Iodide Perovskite Single Crystals", Nov. 29, 2016, The Journal of Physical Chemistry Letters, vol. 7, No. 24, pp. 1-13.

Dujardin et al., "Needs, Trends, and Advances in Inorganic Scintillators", Aug. 2018, IEEE Transactions on Nuclear Science, vol. 65, No. 8, pp. 1977-1996.

Fu et al., "Nanowire Lasers of Formamidinium Lead Halide Perovskites and Their Stabilized Alloys with Improved Stability", Jan. 4, 2016, Nano. Lett., vol. 16, No. 2, pp. 1000-1008.

Gambhir, "Molecular Imaging of Cancer with Positron Emission Tomography", Sep. 2002, Nature Reviews: Cancer, vol. 2, pp. 683-693.

Green et al., "The Emergence of Perovskite Solar Cells", Jul. 2014, Nature Photonics, vol. 8, pp. 506-514.

Gundacker et al., "Measurement of Intrinsic Rise Times for Various L(Y)SO and LuAG Scintillators with a General Study of Prompt Photons to Achieve 10 ps in TOF-PET", Mar. 15, 2016, Phys. Med. Biol., vol. 61, pp. 2255-2264.

Gundacker et al., "State of the Art Timing in TOF-PET Detectors with LuAG, GAGG and L(Y)SO Scintillators of Various Sizes Coupled to FBK-SiPMs", Aug. 8, 2016, Journal of Instrumentation, vol. 11, pp. 1-21.

Hu et al., "High-Performance Flexible Broadband Photodetector Based on Organolead Halide Perovskite", Sep. 11, 2014, Advanced Functional Materials, vol. 24, Issue 46, pp. 1-8.

Isarov et al., "Rashba Effect in a Single Colloidal CsPbBr3 Perovskite Nanocrystal Detected by Magneto-Optical Measurements", Jun. 28, 2017, Nano Lett., vol. 17, pp. 5020-5026.

Jiang et al., "Sensors for Positron Emission Tomography Applications," Nov. 17, 2019, Sensors, vol. 19, Issue 22, pp. 1-56.

Jones et al., "History and Future technical Innovation in Positron Emission Tomography", Jan.-Mar. 2017, Journal of Medical Imaging, vol. 4, Issue 1, pp. 1-17.

Kawano et al., "Scintillating Organic-Inorganic Layered Perovskite-type Compounds and the gamma-ray Detection Capabilities", Nov. 7, 2017, Nature: Scientific Reports, vol. 7, pp. 1-8.

Kim et al., "Printable Organometallic perovskite Enables Large-area, Low-does X-ray Imaging", Oct. 5, 2017, Nature, vol. 550, pp. 87-91.

Kobayashi et al., "Scintillation Characteristics of CsPbCl3 Single Crystals" Jul. 21, 2008, Nuclear Instruments and Methods in Physics Research A, vol. 592, Issue 3, pp. 369-373.

Kraus et al., "Multiple Photon Counting Coincidence (MPCC) Technique for Scintillator Characterisation and its Application to studies of CaWO4 and ZnWO4 Scintillators", Aug. 2, 2005, Nuclear Instruments and Methods in Physics Research A, pp. 522-534.

Lecoq, "Development of New Scintillators for Medical Applications", Feb. 11, 2016, Nuclear instruments and Methods in Physics Research A, vol. 809, pp. 130-139.

Lecoq, "Pushing the Limits in Time-of Flight PET Imaging", IEEE Trans. On Radiation and Plasma Med. Sci., vol. 1, No. 6, pp. 473-484.

Liu et al., "Temperature-dependent Photoluminescence Spectra and Decay Dynamics of MAPbBr3 and MAPbI3 Thin Films", Sep. 12, 2018, AIP Advances, vol. 8, pp. 1-9.

Mikhailik et al., "Luminescence and Scintillation Properties of CsI—A Potential Cryogenic Scintillator", Apr. 2015, Basic Solid State Physics, vol. 252, Issue 4, pp. 804-810.

(56) References Cited

OTHER PUBLICATIONS

Mikhailik et al., "Temperature Dependence of CaMoO4 Scintillation Properties", Sep. 19, 2007, Nuclear Instruments and Methods in Physics Research A, vol. 583, pp. 350-355.
Miyata et al., "Direct Measurement of the Exciton Binding Energy and Effective Masses for Charge Carriers in an Organic-Inorganic Tri-halide Pervoskite", Jun. 15, 2015, Nature Physics, vol. 11, pp. 582-587.
Moller, "Crystal Structure and Photoconductivity of Caesium Plumbohalides", Nov. 22, 1958, Nature, vol. 182, p. 1436.
Moszynski et al., "Energy Resolution and Non-proportionality of the Light Yield of Pure CsI at Liquid Nitrogen Temperatures", Sep. 2003, SCINT Conference, p. 56.
Mykhaylyk et al., "Bright and Fast Scintillation of Organolead Perovskite MAPbBr3 at Low Temperatures", Mar. 7, 2019, Materials Horizons, pp. 1-8.
Mykhaylyk et al., "Low Temperature Scintillation Properties of Ga2O3", Aug. 20, 2019, Appl. Phys. Lett., vol. 115, Issue 8, pp. 1-17.
Radebaugh et al., "Cryocoolers: The State of the Art and Recent Developments", 2009, J. Phys: Condens. Matter, vol. 21, pp. 1-9.
Richter et al., "Enhancing Photoluminescence Yields in Lead Halide Perovskites by Photon Recycling and Light Out-Coupling," Dec. 23, 2016, Nature Communications, vol. 7, pp. 1-8.
Schmidt et al., "Nontemplate Synthesis of CH3NH3PbBr2 Perovskite Nanoparticles", Jan. 3, 2014, Journal of the American Chemical Society, vol. 136, pp. 850-853.
Schmitz et al., "The Physics of PET/CT Scanners", 2013, Imaging Research Lab, p. 1-16.
Seifert et al., "The Lower Bound on the Timing Resolution of Scintillation Detectors", Mar. 13, 2012, Phys. Med. Biol., vol. 57, No. 7, pp. 1797-1814.
Shendrik et al., "Absolute Light Yield Measurements on SrF2 and BaF2 Doped with rare Earth Ions", Jan. 2012, Journal of Latex Class Files, vol. 6, No. 1, pp. 1-5.
Shi et al., "Low Trap-state Density and Long Carrier Diffusion in Organolead Trihalide Perovskite Single Crystals", Jan. 30, 2015, Science: Solar Cells, vol. 347, Issue 6221, pp. 519-521.
Shibuya et al., "Development of Ultra-Fast Semiconducting Scintillators Using Quantum Confinement Effect", Oct. 2004, Japanese Journal of Applied Physics, vol. 43, No. 1 OB, pages L 1333-L 1336.
Stranks et al., "Metal-halide Perovskites for Photovoltaic and Light-emitting Devices", May 7, 2015, Nature Nanotechnology, vol. 10, pp. 391-402.
Schaart et al., "Comparative Study of Co-Doped and Non Co-Doped LSO:Ce and L YSO:Ce Scintillators for TOF-PET", Jun. 2015, IEEE Transactions on Nuclear Science, vol. 62, No. 3, pp. 727-731.
Tyagi et al., "Effect of Codoping on Scintillation and Optical Properties of a Ce-Doped Gd3Ga3Al2O12 Scintillator", Nov. 2013, Journal of Physics D Applied Physics, vol. 46, pp. 1-12.
Van Loef et al., "Crystal Growth and Scintillation Properties of Strontium Iodide Scintillators", Jun. 2009, IEEE Transactions on Nuclear Science, vol. 56, Issue 3, pp. 869-872.
Vandenberghe et al., "Recent Developments in Time-of-flight PET", EJNMMI Physics, vol. 3, Issue 3, pp. 1-30.
Velasquez et al., "Clinical Benefit of High Resolution Breast PET", Feb. 27, 2017, Clinics in Oncology, vol. 2, pp. 1-3.

Voloshinovski et al., "Exciton luminescence of ionic semiconductors CsPbX3 (X=Cl, Br, I)," Ukrainian Journal of Physics, Jan. 1993.
Wakita et al., "Time-resolved Photoluminescence Studies of Free Excitons in CuLnS2 Crystals", May 6, 2002, Applied Physics Letters, vol. 80, No. 18, pp. 3316-3318.
Walrand et al., "Update on Novel Trends in PET/CT Technology and its Clinical Applications", Nov. 25, 2016, Br. J. of Radiol., vol. 91, Issue 1081, pp. 1-10.
Weber, Dieter., "CH3NH3PbX3, ein PB(II)-System Mit Kubischer Perowskitstruktur" 1978, pp. 1443-1445.
Wei et al., "Halide Lead Perovskites for Ionizing Radiation Detection", Mar. 6, 2019, Nature Communications, vol. 10, pp. 1-12.
Wei At Al., "Dopant compensation in alloyed CH3NH3PbBr3-XClx perovskite single crystals for gamma-ray spectroscopy", Nature materials, vol. 16, Jul. 3, 2017, pp. 826-834.
Wei et al., "Sensitive X-ray detectors made of methylammonium lead tribromide perovskite single crystals", Nature Photonics, vol. 10, Mar. 21, 2016, pp. 333-340.
Yakunin et al., "Detection of X-ray Photons by Solution-processed Organic-inorganic Perovskites", Jul. 2015, Nat. Photonics, vol. 9, Issue 7, pp. 444-449.
Zanzonico, "Principles of Nuclear Medicine Imaging: Planar, Spect, Pet, Multi-modality, and Autoradiography Systems", Apr. 2012, Radiation Research vol. 177, pp. 349-364.
Zhang et al., "Photoluminescence Quenching of Inorganic Cesium Lead halides Perovskite Quantum Dots (CsPbX3) by Electron/hole Acceptor", 2017, Phys. Chem. Chem. Phys., vol. 19, pp. 1920-1926.
Saliba, International Patent Application PCT/IB2020/053452, International Search Report and Written Opinion mailed Jul. 13, 2020, 13 pp.
Klamra et al., "Light yield non-proportionality of undoped YAP scintillator," May 15, 2008, IOP Publishing for SISSA, 14 pp.
Mikhailik, et al., "Performance of scintillation materials at cryogenic temperatures," Mar. 11, 2020, Phys. Status Solidi B 247, No. 7, pp. 1583-1599.
Maddalena et al., "Inorganic, Organic, and Perovskite Halides with Nanotechnology for High-Light Yield X- and Y- ray Scintillators," Feb. 8, 2019, Crystals, vol. 9;88, 29 pp.
Saliba, U.S. Appl. No. 16/843,699, Non-Final Office Action mailed Dec. 11, 2020, 9 pp.
Saliba, U.S. Appl. No. 16/843,699, Final Office Action mailed Jun. 17, 2021, 11 pp.
Yakunin, et al., "Detection of gamma photons using solution-grown single crystals of hybrid lead halide perovskites," Sep. 2016, Nature Photonics, 20 pp.
Aozhen et al. "Thermal Quenching and Dose Studies of X-ray Luminescence in Single Crystals of Halide Perovskites" pubs.acs.org, J. Phys. Chem. C, pub. Jun. 26, 2018, 122, p. 16265-16273.
Brunner et al. "A Comprehensive characterization of the time resolution of the Philips Digital Photon Counter", IOP Publishing for Sissa MediaLAB, Jinst, Nov. 8, 2016, p. 1-17.
U.S. Appl. No. 17/688,584, Non-Final Office Action mailed Oct. 6, 2022, 12 pp.
Japanese Patent Application No. 2021-560577, Notice of Reasons for Refusal mailed Oct. 4, 2022, 14 pp.
EPO Application 20720516.2, European Office Action mailed Dec. 5, 2023, 9 pp.

\* cited by examiner

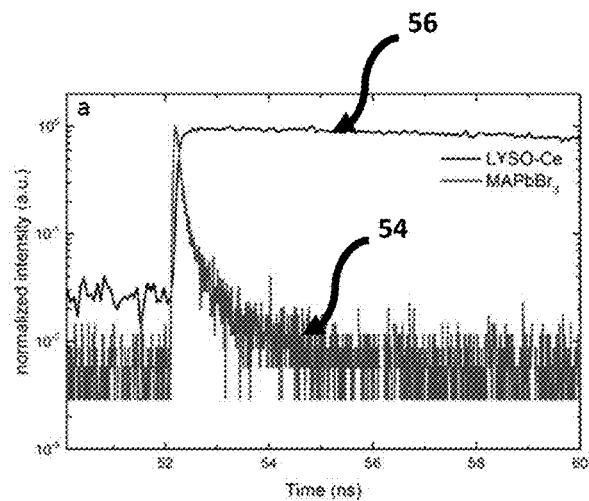
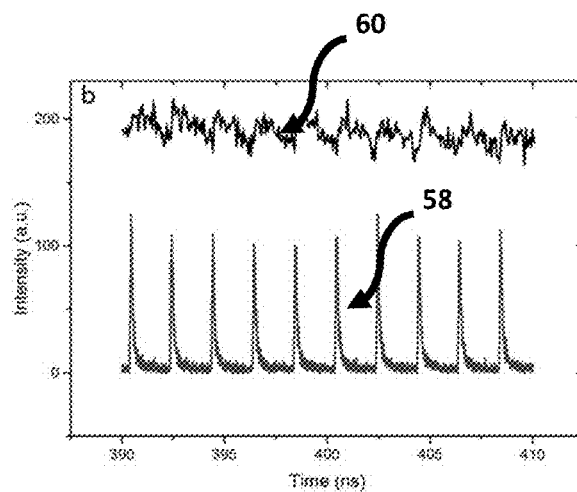
FIG. 8A
FIG. 8B
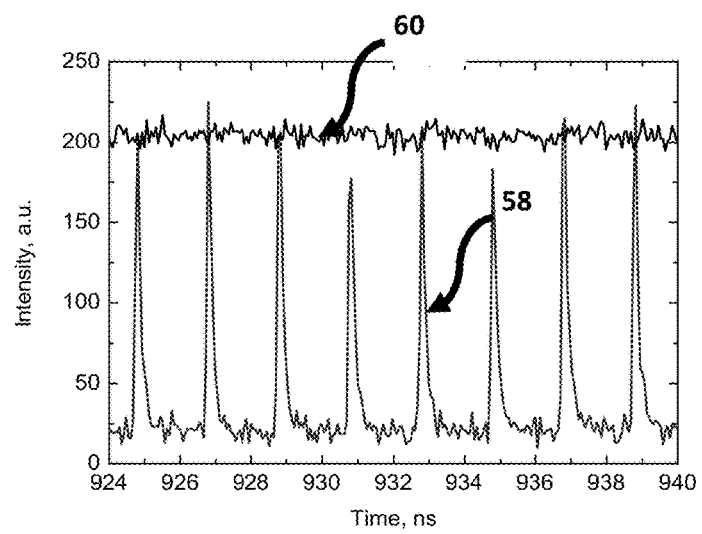
FIG. 8C

LOW-TEMPERATURE PEROVSKITE SCINTILLATORS AND DEVICES WITH LOW-TEMPERATURE PEROVSKITE SCINTILLATORS

RELATED APPLICATIONS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 U.S.C. § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

This application is a continuation of U.S. Non-Provisional patent application Ser. No. 17/688,584 titled "Low-Temperature Perovskite Scintillators and Devices with Low Temperature Perovskite Scintillators" filed on Mar. 7, 2022, which is a continuation of U.S. Non-Provisional patent application Ser. No. 16/843,699, titled "Low-Temperature Perovskite Scintillators and Devices with Low-Temperature Perovskite Scintillators," filed on Apr. 8, 2020 and issued on Mar. 8, 2022 as U.S. Pat. No. 11,269,090, which claims priority to U.S. Provisional Patent Application No. 62/831,992, titled "Bright and Fast Scintillation of Organolead Perovskite MAPbBr3 at Low Temperatures," filed on Apr. 10, 2019, both of which are hereby incorporated by reference in their entireties.

BACKGROUND

Scintillators detect ionizing radiation by converting energy deposited in them to a proportional number of photons. Scintillators are omnipresent in large-scale technical and commercial applications around us. For example, they are found in many branches of physics, security scanners, or medical applications such as nuclear imaging (like tomography) and they typically operate at room temperature.

An ideal scintillator emits a maximum number of scintillation photons per energy deposited, has a high absorption coefficient for gamma quanta, and exhibits a narrow timing profile for its scintillation photons. Brighter and faster scintillators facilitate better timing resolution—which is important for measuring the time of the initial particle or radiation interaction with high precision.

At present, a major limitation of modern scintillators is timing resolution. State-of-the-art resolution in coincidence timing has just broken the 100 ps barrier—with the lowest value of 73±2 ps for LSO-Ce scintillators and 80±4 ps for LGSO-Ce scintillators. A main limitation towards a goal of 10 ps resolution is low light yield and long decay time of scintillators. Currently, the best scintillator in this regard is deemed to be $LaBr_3$—Ce—which exhibits 16 ns decay time and 70000 ph/MeV. To achieve a timing resolution below 10 ps, a scintillator with a light yield of at least 140000 ph/MeV and a decay time of 1 ns, or shorter, is entailed.

Perovskites may have applicability as a scintillator with a light yield of at least 140000 ph/MeV. However, currently-known perovskite scintillators do not have a decay time of 1 ns or shorter. Hybrid metal-halide perovskites such as $CsPbX_3$ (X=Cl, Br or I) have exhibited known semiconducting behavior. In addition, tolerance of optical and electronic characteristics to structural defects made solid-state photovoltaics based on organic-inorganic trihalide perovskites (OTP)—materials with the general formula $MAPbX_3$ where MA=methylammonium, and X=Cl, Br and I—attractive for various optoelectronic applications. Specifically, high photoluminescence quantum yield of OTPs enabled bright light-emitting devices and lasers, whereas high current conversion efficiency upon light exposure underpinned their application as photodetectors. Photovoltaic OTPs have also stimulated solar cell research. However, due to the Shockley-Queisser limit, photovoltaic perovskites are typically tuned to a very narrow band gap range, thereby excluding a majority of high-quality perovskites (especially those with larger band gaps).

Higher-mass elements with a correspondingly high atomic number (Z) used in OTPs, i.e. Pb, Br and I atoms, make OTPs inherently suitable for applications in which good X-ray absorption capability is required. Furthermore, OTPs exhibit a high mobility of charge carriers, which makes them optimal for radiation detection through direct conversion of X-ray photons into current. Soft X-rays (<10 keV) have been detected using the photoelectric effect in polycrystalline $MAPbI_3$ films. Improving the detection probability for hard X-rays (>100 keV) called for a decrease in absorption length. This prompted the development of X-ray detectors based on OTP single crystals or thick films. The energy spectra measured with OTP detectors demonstrated energy resolutions of 35% for 59.6 keV of 241 Am and 6.5% for 662 keV of 137 Cs.

Thus, OTPs may be viable candidates to detect ionizing radiation. It will be appreciated that it may be desirable to avoid limitations that arise from extracting charged particles. This inherent feature of photodetectors with direct photon-to-current conversion imposes two basic constraints. First, it eventually limits the thickness of the absorber and, hence, conversion efficiency for high-energy photons. Second, the transit time of charge carriers in the material dictates the relatively slow (~100 μs) response time of OTP photodetectors. It will be appreciated that an advantage of a scintillation detector is non-reliance on extracting charged particles from the material. That is, light can be detected from the bulk of the crystal absorber with a response time governed by the probability of radiative decay of excited particles—and this can be very fast (as is the case for exciton emission).

It will be appreciated that fully inorganic perovskites may have properties as scintillators. As an example, nanosecond X-ray luminescence of free excitons in $CsPbX_3$ (X=Cl, Br, I) at 77 K has been observed—but light yield at room temperature was <500 ph/MeV. Sub-nanosecond scintillation decay at room temperature was found in layered hybrid metal-halide compound $(C_6H_{13}NH_3)_2PbI_4$—but with a light yield of only—6000 ph/MeV. Light yields of 9000 and 14000 ph/MeV have been reported for layered perovskites (EDBE)PbCl$_4$ (EDBE=2,2'-ethylenedioxy)bis(ethylamine)) and (C$_6$H$_5$C$_2$H$_4$NH$_3$)$_2$PbBr$_3$.

However, even with research into OTPs as possible room temperature scintillators with timing resolution below 10 ps—a scintillator with a light yield of at least 140000 ph/MeV and a decay time of 1 ns or shorter has remained unachievable in the currently-known art. Moreover, research into performance of OTPs as possible low temperature scintillators has found that that decay times are worse at low temperature for all OTPs.

SUMMARY

Disclosed embodiments include perovskite scintillators configured to be operated at a low temperature, detectors with perovskite scintillators configured to be operated at a low temperature, scanners with perovskite scintillators configured to be operated at a low temperature, methods of cooling a perovskite scintillator to a low temperature, and methods of configuring a perovskite scintillator to be operated at a low temperature.

In an illustrative embodiment, an apparatus includes a perovskite scintillator configured to be operated at a low temperature.

In another illustrative embodiment, a detector includes a source of ionizing radiation. A perovskite scintillator is configured to be irradiated by ionizing radiation at a first frequency from the source of ionizing radiation and emit photons responsive thereto at a second frequency that is lower than the first frequency, the perovskite scintillator being further configured to be operated at a low temperature. A cooling system is configured to cool the perovskite scintillator to the low temperature. A photodetector is configured to detect photons emitted by the perovskite scintillator.

In another illustrative embodiment, a scanner includes a perovskite scintillator configured to be irradiated by pairs of gamma photons at a first frequency and emit photons responsive thereto at a second frequency that is lower than the first frequency, the perovskite scintillator being further configured to be operated at a low temperature. A cooling system is configured to cool the perovskite scintillator to the low temperature. A photodetector is configured to detect photons emitted by the perovskite scintillator.

In another illustrative embodiment, a method includes cooling a perovskite scintillator to a low temperature and irradiating the cooled perovskite scintillator with ionizing radiation.

In another illustrative embodiment, a method includes configuring a perovskite scintillator to be cooled to a low temperature.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 8A is a graph that illustrates normalized scintillation decay curves in a perovskite scintillator and a LYSO scintillator.

FIGS. 8B and 8C are graphs of a sequence of X-ray pulses as recorded by a photon counter using a perovskite scintillator and a LYSO scintillator.

The use of the same symbols in different drawings typically indicates similar or identical items unless context dictates otherwise.

DETAILED DESCRIPTION

Figure 1A:
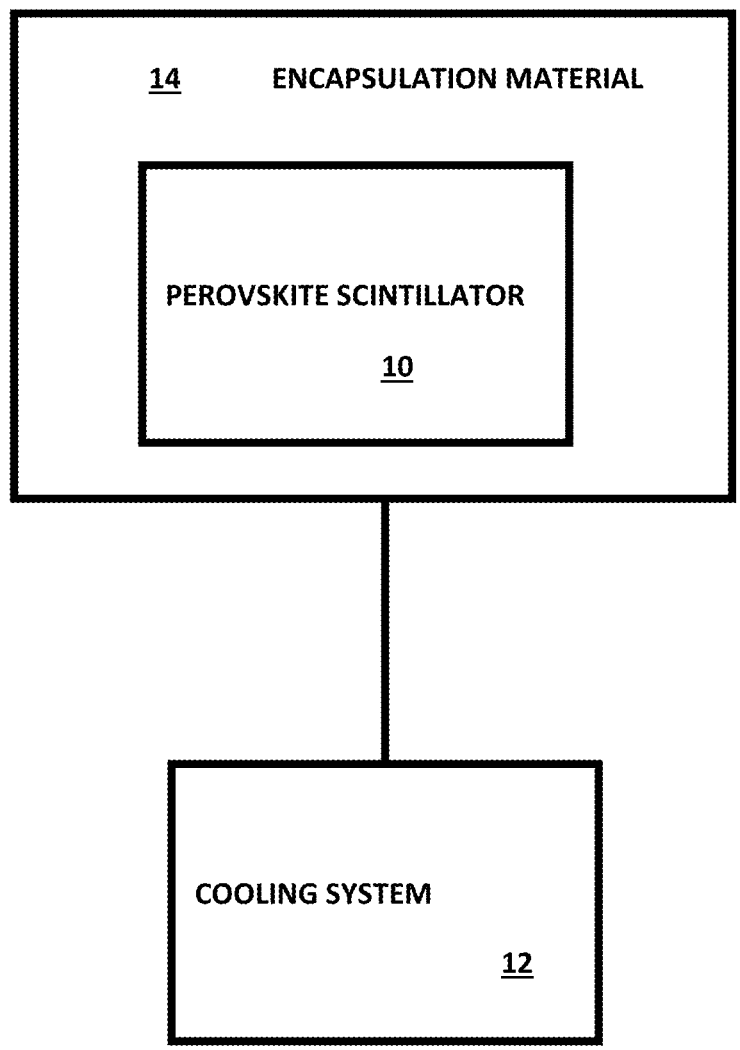
FIG. 1A is a block diagram of an illustrative perovskite scintillator configured to be operated at a low temperature.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Given by way of overview, various disclosed embodiments include perovskite scintillators configured to be operated at a low temperature, detectors with perovskite scintillators configured to be operated at a low temperature, scanners with perovskite scintillators configured to be operated at a low temperature, methods of cooling a perovskite scintillator to a low temperature, and methods of configuring a perovskite scintillator to be operated at a low temperature.

Referring to FIG. 1A, in various embodiments an illustrative perovskite scintillator 10 is configured to be operated at a low temperature. As will be explained below, by flying in the face of the prior art and by being configured to be operated at a low temperature, in various embodiments the perovskite scintillator 10 may be able to achieve a combination of light yield and decay time that has not been achievable in the prior art.

Now that an overview has been provided, details will be provided by way of non-limiting examples that are given by way of illustration only and not of limitation.

Still referring to FIG. 1A, in various embodiments the perovskite scintillator 10 may include the entire material range of perovskites. To that end, the perovskite scintillator 10 may include any perovskite, such as, for example, without limitation a perovskite such as an organic-inorganic trihalide perovskite or an inorganic trihalide perovskite. As is known, a perovskite has a general structure of $AMX_3$ where:

A includes inorganic cations Ai and inorganic cations Ao. The inorganic cations Ai are independently selected from $Li^+$, $Na^{3O}$, $K^{3O}$, $Rb^+$, $Cs^+$, or $Tl^+$, and the organic cations Ao are independently selected from ammonium ($NH_4^+$), methyl ammonium (MA) ($CH_3NH_3^+$), ethyl ammonium ($CH_3CH_2NH_3^+$, formamidinium (FA) ($CH(NH_2)_2^+$), methylformamidinium ($CH_3C(NH_2)_2^+$), guanidium ($C((NH)_2)_3^+$), tetramethylammonium (($CH_3)_4N^+$), dimethylammonium (($CH_3)_2NH_2^+$), or trimethylammonium (($CH_3)_3NH^+$). A may also include Au, Ag, or Cu.

M is selected from $Cu_{2+}$, $Ni_{2+}$, $Co^{2+}$, $Fe_{2+}$, $Mn^{2+}$, $Cr^{2+}$, $Pd_{2+}$, $Cd^{2+}$, $Ge^{2+}$, $Sn^{2+}$, $Pb^{2+}$, $Eu^{2+}$, $Yb^{2+}$ or a combination thereof. M may also include metal mixtures such as AgBi.

X is an anion independently selected from $Br^-$, $I^-$, $Cl^-$, $SCN^-$, $CN^-$, $NC^-$, $OCN^-$, $NCO^-$, $NCS^-$, $SeCN^-$, $TeCN^-$, $PF_6^-$, $BF_4^-$ or a combination thereof.

Still referring to FIG. 1A, in various embodiments the perovskite scintillator 10 includes an organic-inorganic trihalide perovskite ("OTP") scintillator. In some such embodiments, the OTP scintillator may include an $MAPbBr_3$ scintillator. In other such embodiments, the OTP scintillator may include an $MAPbI_3$ scintillator or an $MAPbCl_3$ scintillator. However, it will be appreciated that the perovskite scintillator 10 is not limited to an OTP scintillator or an $MAPbBr_3$ scintillator. That is, the perovskite scintillator 10 may include the entire material range of perovskites as discussed above.

In various embodiments, timing resolution of the perovskite scintillator 10 is at most 10 ps. In such embodiments, light yield of the perovskite scintillator 10 is at least 140000 ph/MeV and decay time of the perovskite scintillator IO is at most I ns. Details regarding light yield and decay time of the perovskite scintillator 10 as a function of cooling to cryogenic temperatures will be discussed further below.

Still referring to FIG. 1A, in various embodiments a cooling system 12 is configured to cool the perovskite scintillator to the low temperature. In some such embodiments, the cooling system 12 includes a cryogenic cooling system. The cooling system 12 may be any suitable cryogenic cooling system as desired. For example, the cooling system 12 may include a suitable Stirling Cryogenerator available from Stirling Cryogenics, Son, Netherlands. It will be appreciated that cryogenic cooling systems are well known and, as a result, details of their construction and operation need not be provided for an understanding of disclosed subject matter.

To that end, in various embodiments the low temperature is less than 273 K. In some such embodiments, the low temperature is between about 50 and 130 K, and in some such embodiments the low temperature is about 77 K. As mentioned previously, temperature-dependent behavior of the perovskite scintillator 10 is explained in detail further below.

Figure 1B:
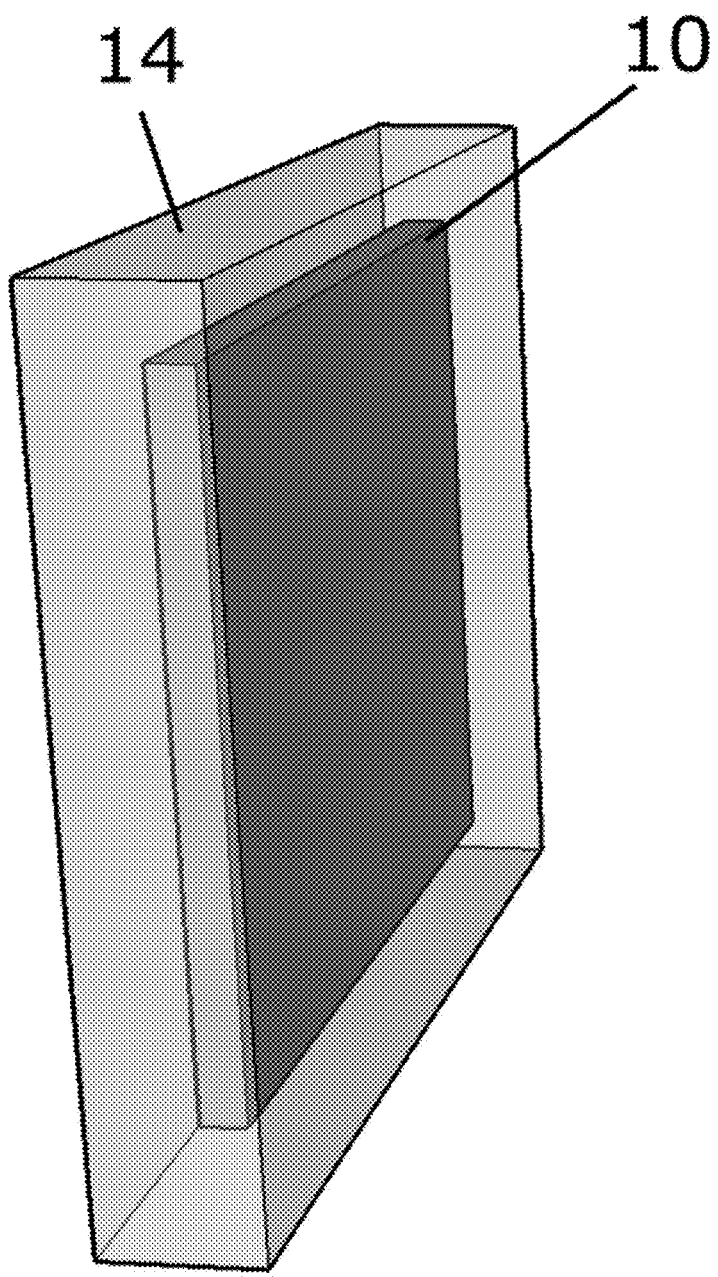
FIGS. 1B and 1C are perspective views of details of the perovskite scintillator of FIG. 1A.
Figure 1C:
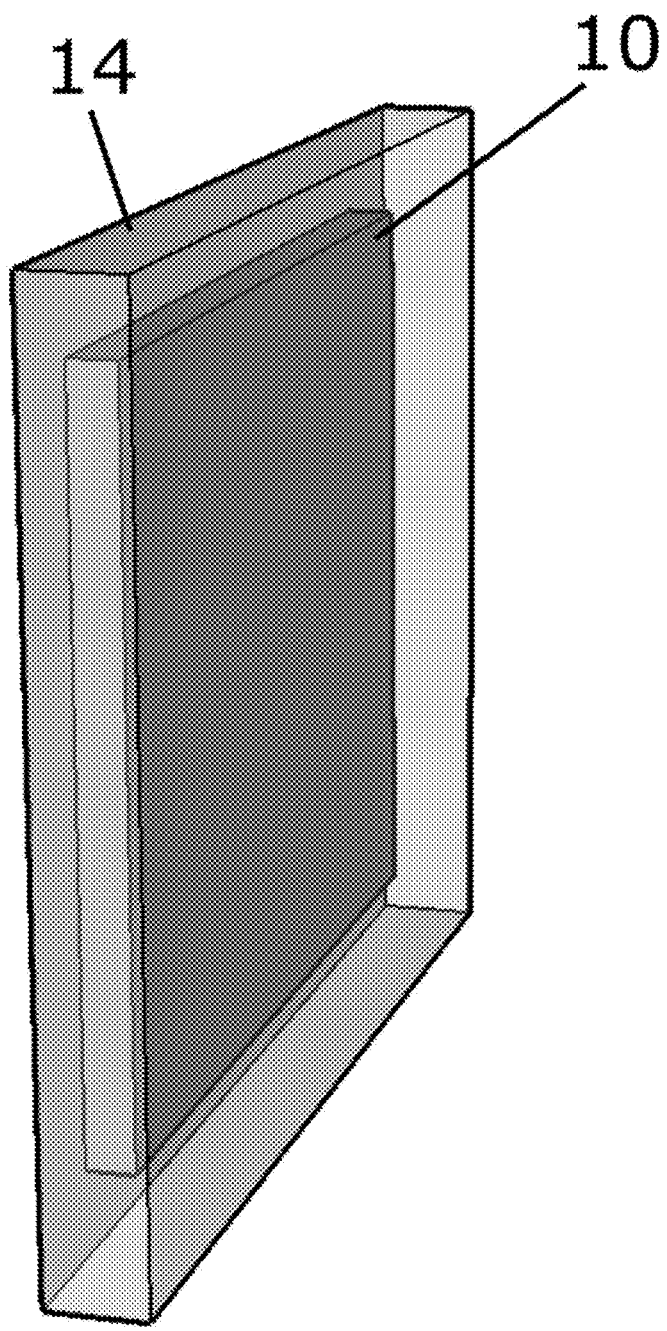

As mentioned above, the perovskite scintillator 10 is configured to be operated at the low temperature. As is known, perovskites are hygroscopic and exposure to moisture and oxygen can contribute to degradation of their performance. To that end and referring additionally to FIGS. 1B and 1C, in various embodiments the perovskite scintillator 10 may be encapsulated in encapsulation material 14. It will be appreciated that, as shown in FIGS. 1B and 1C, the encapsulation material 14 may be disposed in any manner desired to suitably encapsulate the perovskite scintillator 10.

In some such embodiments the encapsulation material 14 may include a film of material such as $SiO_2$, $Al_2O_3$, SiN, other oxides, or other nitrides. In such embodiments, the film may be a thin film that is deposited via a process such as chemical vapor deposition ("CVD"), atomic layer deposition ("ALD"), physical vapor deposition ("PVD"), or the like.

In some other such embodiments the encapsulation material 14 may include epoxies, polymers, ultraviolet-curable polymers, waxes or the like.

In some other such embodiments the encapsulation material 14 may include glass. In some such embodiments, glass encapsulation or other protective layers may be glued to the perovskite scintillator 10. In some other such embodiments, the perovskite scintillator 10 may be encapsulated in a glass vial.

In some other such embodiments the encapsulation material 14 may include a two-dimensional material such as, without limitation, graphene, hexagonal boron nitride (h-BN), $MoS_2$, or the like.

In some other such embodiments the encapsulation material 14 may include a moisture/oxygen getter material.

Figure 2A:
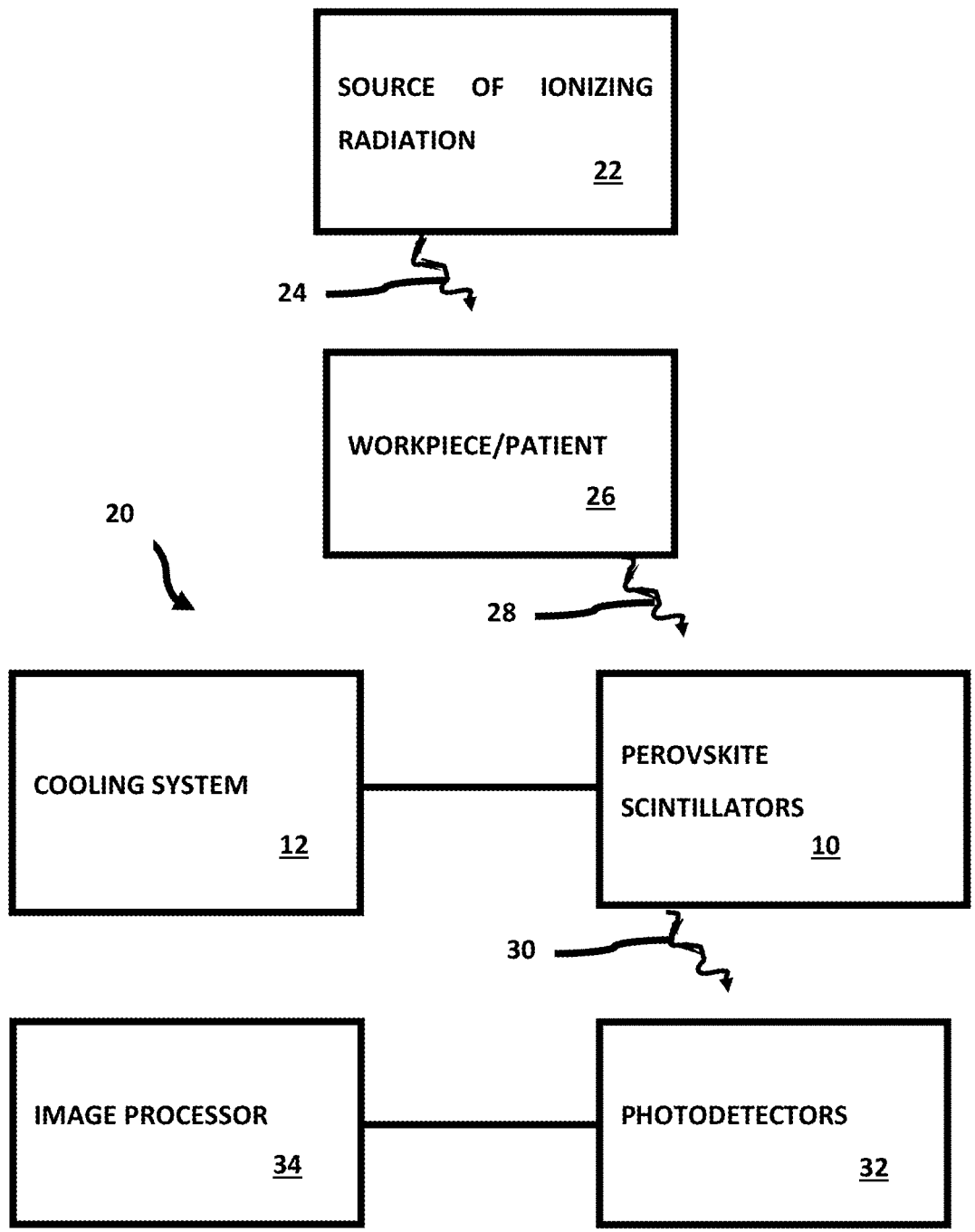
FIG. 2A is a block diagram of an illustrative detector with perovskite scintillators of FIG. 1A configured to be operated at a low temperature.

It will be appreciated that the perovskite scintillator IO is suited for use in various imaging systems, such as various detectors and scanners. Referring additionally to FIG. 2A, in various embodiments the perovskite scintillator 10 may be configured to be operated as part of a detector 20. It will be appreciated that in some embodiments the detector 20 may be an X-ray detector such as, without limitation, a medical X-ray detector, a security X-ray detector, a manufacturing inspection X-ray detector, a homeland security detector, a nuclear camera, or the like. It will be further appreciated that in some other embodiments the detector 20 may be a gamma ray detector such as, without limitation, a medical gamma ray detector, a security gamma ray detector, a nondestructive testing radiography gamma ray or x-ray detector, a petroleum industrial gamma ray detector, or the like.

Figure 2B:
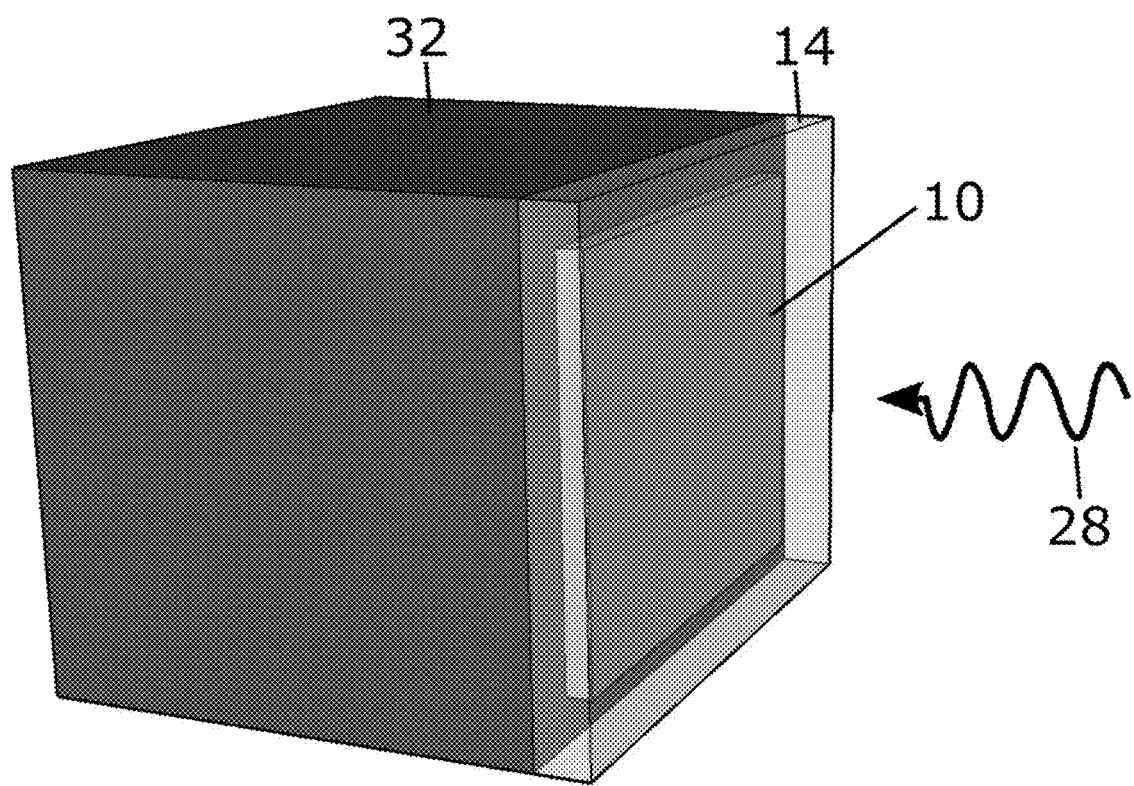
FIG. 2B illustrates details of the detector of FIG. 2A.

In various embodiments, the detector includes a source 22 of ionizing radiation 24. The perovskite scintillators 10 are configured to be irradiated by ionizing radiation 28 at a first frequency from the source 22 of ionizing radiation 24 and emit photons 30 responsive thereto at a second frequency that is lower than the first frequency. The perovskite scintillators 10 are further configured to be operated at the low temperature. The cooling system 12 is configured to cool the perovskite scintillators 10 to the low temperature. Referring additionally to FIG. 2B, photodetectors 32 are configured to detect photons emitted by the perovskite scintillators 10.

Details of the detector 20 are set forth below by way of illustration and not of limitation. It will be appreciated that the detector 20 is illustrative and may include an X-ray detector (such as without limitation those described above) or a gamma ray detector (such as without limitation those described above).

A suitable source 22 emits ionizing the radiation 24. In some embodiments the source 22 may be an X-ray generator and the ionizing radiation 24 may be X-rays as desired for a particular application. In some other embodiments the source 22 may be a gamma ray source and the ionizing radiation 24 may be gamma rays as desired for a particular application. Regardless, X-ray generators and gamma ray sources are well known and details of their construction and operation are not necessary for an understanding of disclosed subject matter.

A workpiece or patient 26 is exposed to the ionizing radiation 24. Some of the ionizing radiation 26 is absorbed by the workpiece or patient 26. Ionizing radiation 28 that is not absorbed by the workpiece or patient 26 is transmitted through the workpiece or patient 26. It will be appreciated that the workpiece or patient 26 is not considered to be part of the detector 20.

The detector 20 includes the perovskite scintillators 10 that are configured to be operated at the low temperature. The perovskite scintillators 10 are exposed to and are irradiated by the ionizing radiation 28 that is transmitted through the workpiece or patient 26. The perovskite scintillators 10 absorb high-energy photons from the ionizing radiation 28, down-convert them into the photons 30 (typically in the visible light frequency range), and emit the photons 30. Thus, the perovskite scintillators 10 are irradiated by the ionizing radiation 28 at a first frequency and emit the photons 30 responsive thereto at a second frequency that is lower than the first frequency. The perovskite scintillators 10 have been described above and their performance with respect to temperature will be discussed further below. While present in various embodiments, for purposes of clarity the encapsulation material 14 (FIGS. 1B and 1C) is not shown in FIG. 2. The encapsulation material 14 has been discussed above. Accordingly, further discussion of details of the perovskite scintillators 10 or the encapsulation material 14 is not needed for an understanding of the detector 20.

The cooling system 12 is thermally coupled to the perovskite scintillators 10 for cooling the perovskite scintillators 10 to the low temperature. The cooling system 12 and the low temperature have been discussed above. Accordingly, further discussion of details of the cooling system 12 or the low temperature is not needed for an understanding of the detector 20.

The photodetectors 32 are configured to detect the photons 30. In various embodiments the photodetector 32 may include a photomultiplier, a photomultiplier tube, a microchannel plate photomultiplier, a silicon photomultiplier, an avalanche photodiode, a cadmium zinc telluride detector, a single-photon avalanche diode, a digital silicon photomultiplier, or the like.

Depending on the type of photodetector, performance of the photodetector 32 may be affected (that is, may be enhanced or may be adversely affected) by cooling. Because the perovskite scintillators 10 are to be cooled to the low temperature, the photodetectors 32 may take advantage of this by also being cooled—although potentially to a different temperature. As such, in various embodiments the photodetectors 32 may be thermally isolated from the perovskite scintillators 10—or in some cases perhaps even heated. Thus, in various embodiments the photodetector 32 is configured to be cooled to a cooled temperature. In some embodiments the cooled temperature may be different from the low temperature. In some embodiments the cooled temperature may be higher than the low temperature.

In various embodiments, the photodetector 32 may have a coincidence resolving time of less than 1,000 ps as desired for a particular application. In some such embodiments, the photodetector 32 may have a coincidence resolving time of less than 10 ps as desired for a particular application.

In various embodiments an image processor 34 is coupled to receive and is configured to process signals that are output by the photodetectors 32. The image processor 34 may be any suitable computer-based image processor, image processing sub-system, or image processing system known in the art. Image processors for detectors (like X-ray detectors and gamma ray detectors) are well known in the art, and details of their construction and operation are not necessary for an understanding of disclosed embodiments.

Figure 3:
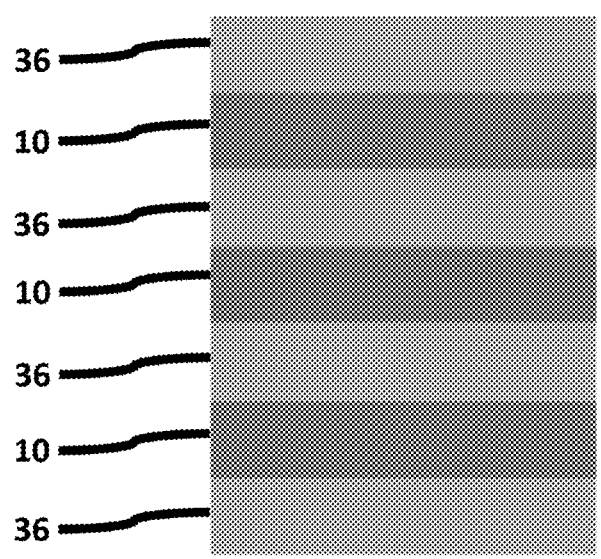
FIG. 3 is a side plan view in partial schematic form of another illustrative perovskite scintillator configured to be operated at a low temperature.

Referring additionally to FIG. 3, in various embodiments several scintillators may be combined in such a way to improve the combined scintillator performance. In some such embodiments, the detector 20 (FIG. 2) may include at least one non-perovskite scintillator 36 that is disposed adjacent the perovskite scintillator 10 and that is configured to be irradiated by the ionizing radiation 28 at the first frequency and to emit photons responsive thereto at the second frequency that is lower than the first frequency. In such embodiments, the photodetectors 32 are further configured to detect the photons emitted by the non-perovskite scintillator 36.

It will be appreciated that, in various embodiments, the perovskite scintillator 10 may have a fairly low density (approximately in the range of 3-4.7 g cm^3) and a low atomic number (Z number) compared to other scintillators—such as BGO, LYSO, LSO, and the like. It will be further appreciated that a density of 7 g cm^3 or more may be preferable for some applications. As is known, density or Z number (atomic number) directly correlates to the X-ray stopping power of a scintillator. Thus, in various applications high stopping power or otherwise very thick crystals may be entailed—which may not be optimal for some applications.

To address such applications, in various embodiments the perovskite scintillator 10 may be combined with the non-perovskite (that is, high Z) scintillators 36 to take advantage of the fast response of the perovskite scintillators 10 and the high stopping power of the high Z scintillators 36 to potentially obtain advantages of both types of scintillators. In various embodiments, such combinations of scintillators may be in the form of stacks wherein the perovskite scintillators 10 and the high Z scintillators 36 may be stacked several times on top of each other (or next to each other) or in other more complex configurations. In some such embodiments, the detector 20 may include the perovskite scintillators 10 and the non-perovskite scintillators 36, wherein single ones of the perovskite scintillators 10 are disposed adjacent single ones of the non-perovskite scintillators 36. In some such embodiments, air (or other material) may be disposed between the alternating scintillators IO and 36 to help reduce light sharing.

As such, in some embodiments the non-perovskite scintillator 36 may include a high atomic number (high Z) scintillator. In some such embodiments, the high atomic number scintillator 36 may be made from bismuth germanate, lutetium oxyorthosilicate, and/or lutetiumyttrium oxyorthosilicate.

In some such embodiments, the perovskite scintillator 10 and/or the non-perovskite scintillator 36 may be configured in a form such as a plate, a line, a square, a circle, and/or a particle. In some such embodiments, one scintillator may be embedded in the other scintillator. In some such embodiments, the perovskite scintillator 10 and/or the non-perovskite scintillator 36 may be defined in a topological space such as zero-dimensional ("0D"), one-dimensional ("1D"), and/or two-dimensional ("2D"). In some such embodiments, the perovskite scintillator 10 and/or the non-perovskite scintillator 36 may be defined in a form such as nanorods, quantum dots, and/or nanocrystals.

In some such embodiments, the detector 20 may include the perovskite scintillators 10 and the non-perovskite scintillators 36. In such embodiments, single ones of the perovskite scintillators 10 may be disposed adjacent single ones of the non-perovskite scintillators 36. It will be appreciated that different types of the non-perovskite scintillators 36 (as discussed above) may be used. It will be appreciated further that the stacking configuration may be repeated several times (as shown in FIG. 3).

Figure 4A:
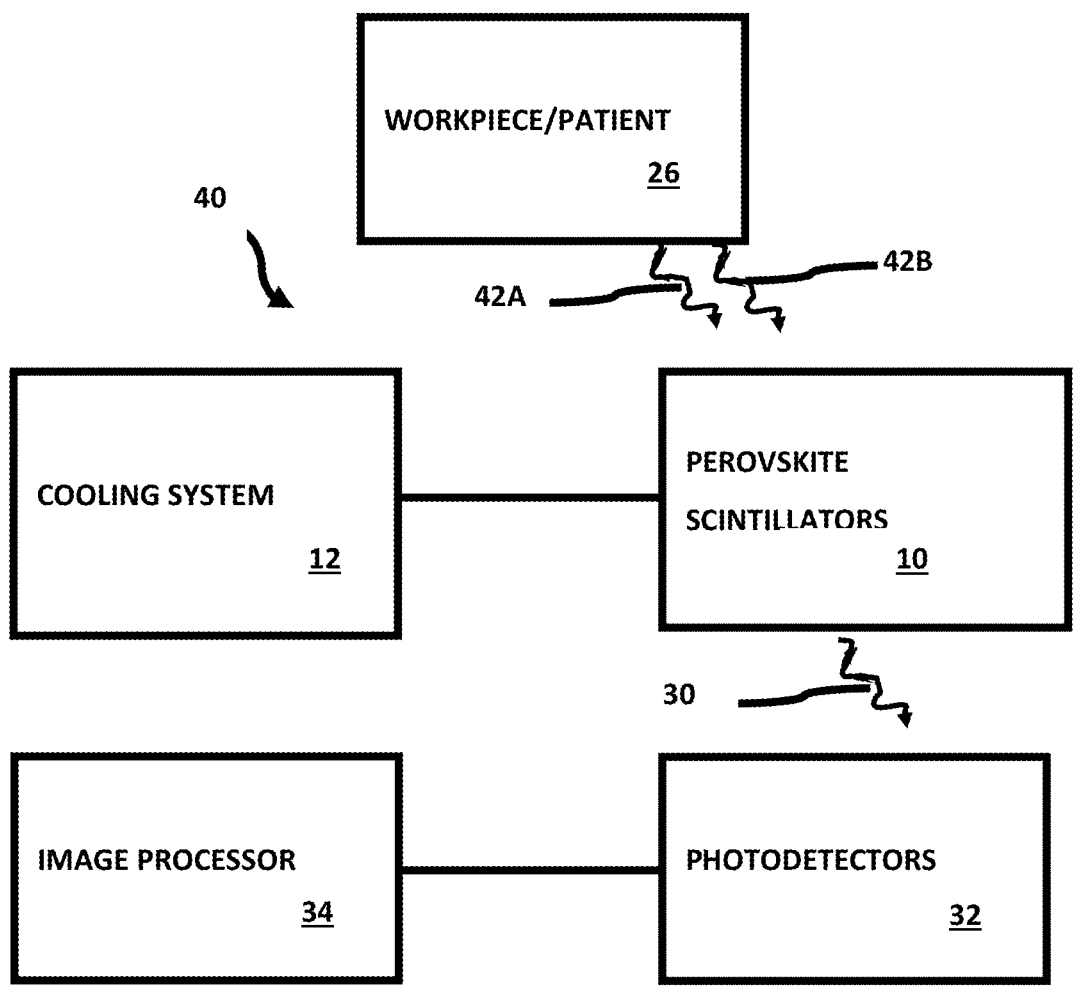
FIG. 4A is a block diagram of an illustrative scanner with perovskite scintillators of FIG. 1A configured to be operated at a low temperature.

Referring additionally to FIG. 4A, in various embodiments the perovskite scintillator 10 may be configured to be operated as part of a scanner 40. In some embodiments the scanner 40 may be a tomography scanner such as, without limitation, a positron-emission tomography ("PET") scanner, a computed tomography ("CT") scanner, or the like. In some other embodiments the scanner 40 may be a scanner such as, without limitation, a scanning electron microscope, an X-ray powder diffraction system, an X-ray photoelectron spectroscope, a particle detector, or the like.

In various embodiments the scanner 40 includes the perovskite scintillator 10 configured to be irradiated by pairs of gamma photons 42A and 42B at a first frequency and emit the photons 30 responsive thereto at a second frequency that is lower than the first frequency. The perovskite scintillator 10 is further configured to be operated at the low temperature. The cooling system 10 is configured to cool the perovskite scintillator 10 to the low temperature. The photodetector 32 is configured to detect the photons 30 emitted by the perovskite scintillator 10.

Details of the scanner 40 are set forth below by way of illustration and not of limitation. It will be appreciated that the scanner 40 is illustrative and may include without limitation the scanners described above. For purposes of brevity, details regarding the scanner 40 will be explained below with respect to an illustrative tomography scanner (in particular, an illustrative PET scanner) given by way of illustration only and not of limitation. Details regarding the perovskite scintillators 10, the cooling system 12, and the photodetectors 32 have been set forth above and need not be repeated for an understanding of disclosed subject matter.

Figure 4B:
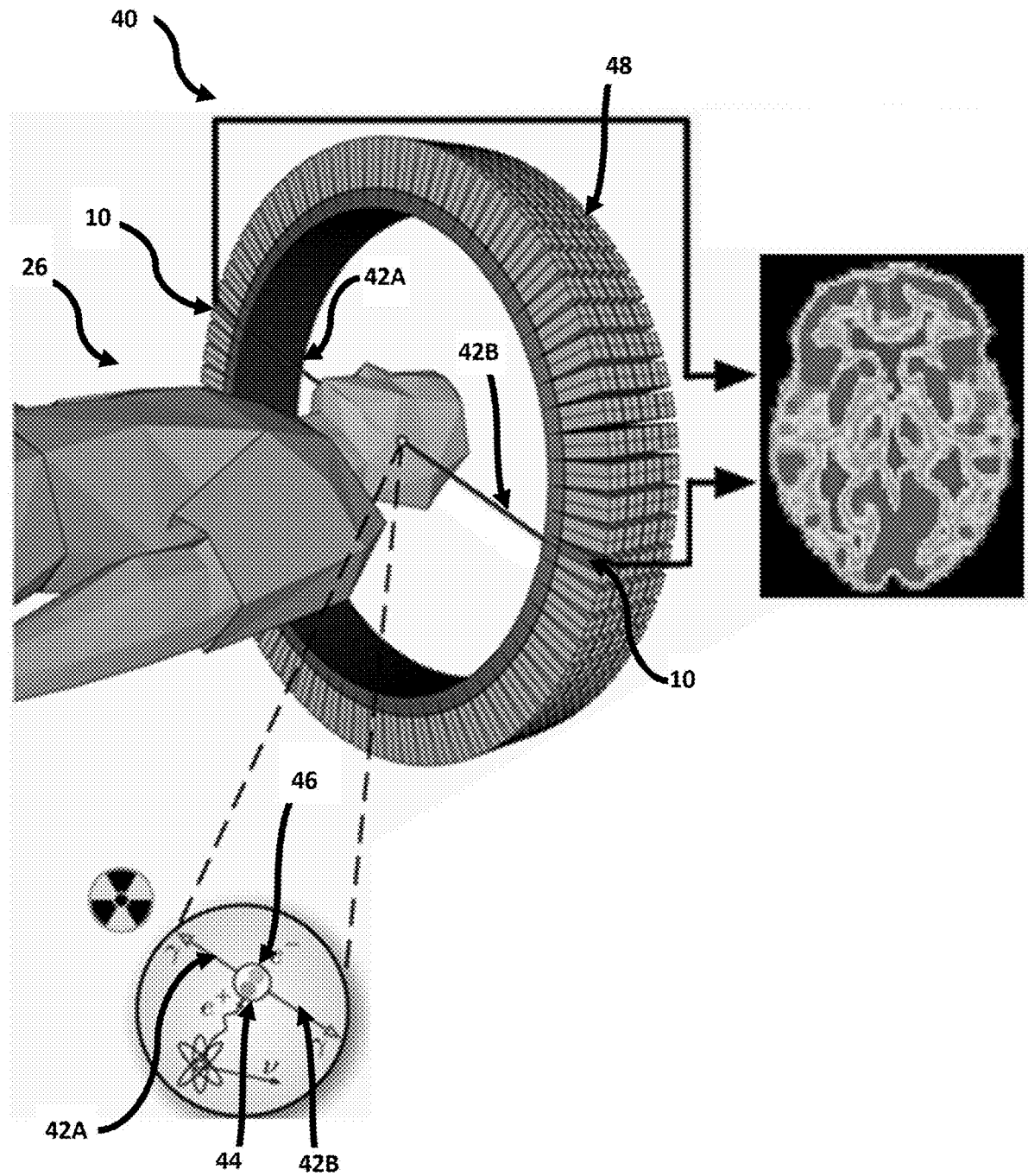
FIGS. 4B-4D illustrate details of the scanner of FIG. 4A.
Figure 4C:
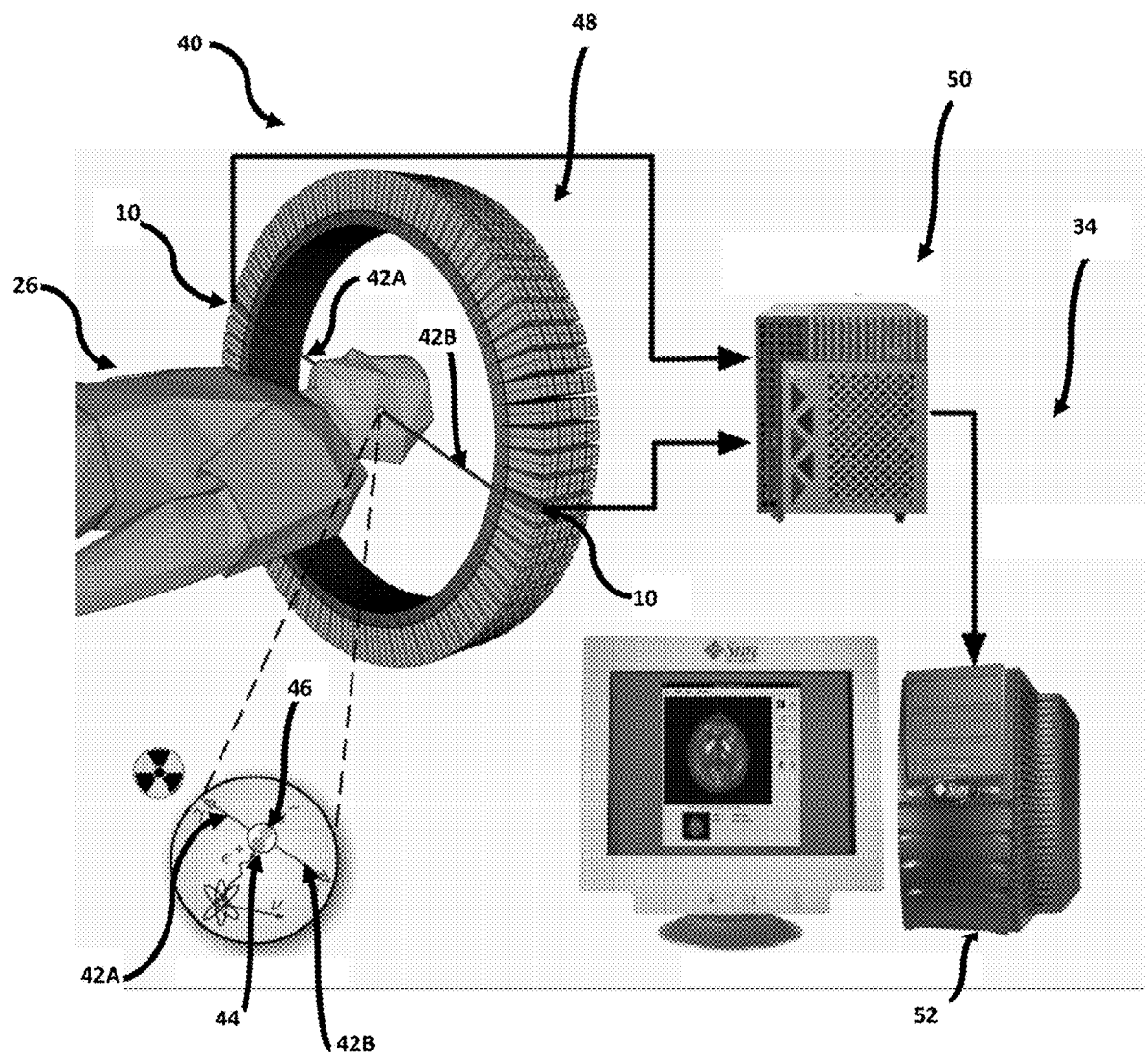
Figure 4D:
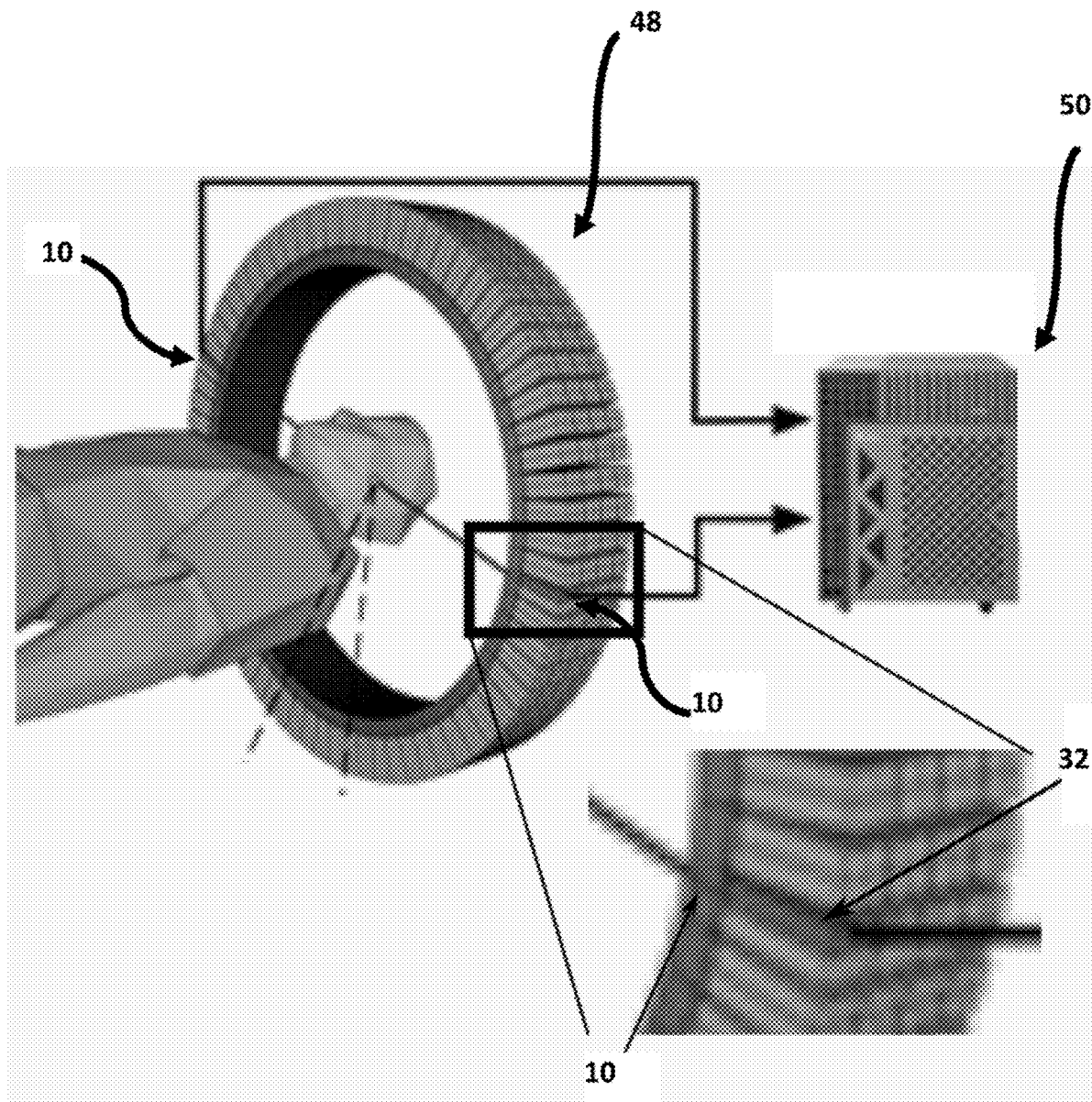

Referring additionally to FIGS. 4B, 4C, and 4D, in various embodiments a radioactive tracer (not shown) is injected into the body of the patient 26. As is known, a tracer isotope is chemically attached to a biological active molecule specific to the disease to be measured. The radioactive tracer circulates in the body of the patient 26 and accumulates on target cells (such as, for example, a cancerous cell). The patient 26 is inserted into the PET scanner 40.

As the radioisotope undergoes positron decay it emits a positron 44 (FIGS. 4B and 4C). The positron 44 decelerates and eventually interacts with an electron 46 (FIGS. 4B and 4C). The encounter annihilates both the positron 44 and the electron 46, thereby producing the pair of annihilation (gamma) photons 42A and 42B that move in approximately opposite directions (as shown in FIGS. 4B and 4C).

The two gamma photons 42A and 42B are detected by the perovskite scintillators 10 arranged in a ring 48 in the detector 40. Due to their high energy, the gamma photons 42A and 42B are difficult to be detected by conventional detectors and therefore the perovskite scintillators 10 are used to down convert the frequency of the gamma rays 42A and 42B to a frequency suitable for the photodetectors 32 (typically in the visible frequency range).

In various embodiments, the image processor 34 is coupled to receive and is configured to process signals that are output by the photodetectors 32. In various embodiments the image processor 34 includes a coincidence processing unit 50 and an image reconstruction unit 52.

The coincidence processing unit 50 is configured to localize the positron annihilation event. In some embodiments the coincidence processing unit 50 may be configured to localize the source of the positron annihilation event along a straight line of coincidence (also referred to as a line of response—or "LOR"). In embodiments in which the resolving time of the perovskite scintillators 10 is less than 500 picoseconds, it may be possible to localize the positron annihilation event to a segment of a chord (whose length is determined by the timing resolution of the perovskite scintillators 10). As the timing resolution improves, it will be appreciated that the signal-to-noise ratio (SNR) of the image will improve, thereby entailing fewer positron annihilation events to achieve the same image quality.

In some other embodiments the coincidence processing unit 50 may be configured to determine an approximate position of the positron annihilation event along the line of response using measured difference in arrival times of the gamma photons 42A and 42B. Such localization is referred to as time-of-flight positron emission tomography ("TOF-PET"). As is known, TOF-PET can help improve image quality and can help reduce image acquisition time.

TOF-PET can be enabled in systems in which scintillator decay time is at most around 3 ns. It will be appreciated that embodiments in which the perovskite scintillators 10 are cooled to the low temperature and decay time is at most 1 ns lend themselves to TOF-PET applications. It will be appreciated that coincidence resolving time for photodetectors in TOF-PET applications should be on the order of hundreds of ps or, more desirably, in the single digit ps range.

The estimated time-of-flight difference ($\Delta t$) between arrival times of the photons 42A and 42B at their respective perovskite scintillators 10 can allow localization (with a certain probability) of the positron annihilation event on the line of response. The distance $\Delta x$ to the origin of the ring 48 of a location of the positron annihilation event on the line of response is proportional to the time-of-flight difference $\Delta t$ according to the relationship $$\Delta x = \frac{c\Delta t}{2}$$

where c is the speed of light.

In various embodiments the image reconstruction unit 52 may be configured to pre-process data and reconstruct images from projections. In various embodiments, the image reconstruction unit 52 may be configured to reconstruct images using suitable techniques as desired such as: filtered-back projection; statistical, likelihood-based iterative expectation-maximization algorithms (such as without limitation the Shepp-Vardi algorithm); Bayesian methods that involve a Poisson likelihood function and an appropriate prior-probability (for example, a smoothing prior leading to total variation regularization or a Laplacian distribution leading to $l_1$-based regularization in a wavelet or other domain), such as via Grenander's Sieve estimator or via Bayes penalty methods or via Good's roughness method; or the like.

Figure 5:
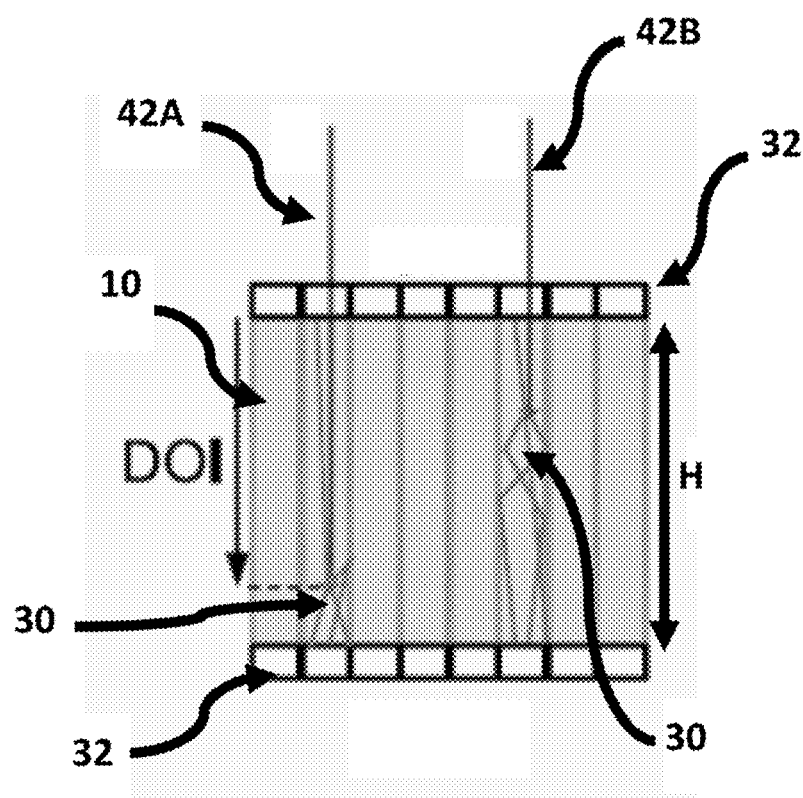
FIG. 5 is a side plan view in partial schematic form of another illustrative perovskite scintillator.

It will be appreciated that resolution of scintillators may be limited by scintillator thickness. Referring additionally to FIG. 5, a gamma ray photon 42 (either 42A or 42B strikes the perovskite scintillator 10 and causes emission of the photons 30. However there can be an uncertainty regarding where in the perovskite scintillator 10 the gamma ray photon 42 hits the atom of the perovskite scintillator 10. In some cases, this uncertainty can cause a scintillator-limited-thickness resolution given by the relationship $$\Delta t = H/c$$

where
Δt is scintillator-limited-thickness resolution;
H is scintillator thickness; and
c is the speed of light.

In various embodiments, this scintillator-limited-thickness resolution is resolved by use of multiple photodetectors 32. In some such embodiments, one photodetector 32 is disposed on one side (such as at the top) of the perovskite scintillator 10 and another photodetector 32 is disposed on another side (such as at the bottom) of the perovskite scintillator 10. Thus, with use of two photodetectors 32 the position of the scintillation event can be resolved and this uncertainty can be reduced.

Details regarding performance of the perovskite scintillator 10 (such as decay time and light yield) as a function of temperature will be explained below. In short, at lower cryogenic temperatures (such as those toward the temperature of liquid nitrogen and below), perovskite crystals can show scintillation properties in terms of high signal output and quick response time. These scintillation properties of perovskite scintillators were measured at such temperatures using a multi-photon counting technique (and specifically—scintillation time constants were determined using pulsed monochromatic 14 keV X-rays from synchrotron radiation).

As an initial observation, the entire material range of perovskites may be considered for use in scintillators due to independence from the band gap. As is known, scintillators absorb high-energy radiation, far exceeding their band gap, and then emit photons. Thus, band gap tuning (that is entailed for solar cells—which are therefore limited to a narrow range of perovskites) is not entailed for scintillators. As a result, the entire material range of perovskites can be opened for scintillation—irrespective of the band gap.

As another initial observation, perovskites contain elements with a high atomic number (high Z)—for example, Cs, Pb, I, or B. This high atomic number can help render perovskites as attractive scintillation materials because the cross-section—and therefore scintillation—increases with $Z^4$.

In an investigation of performance of perovskite scintillators at low temperatures, it was found that between 50 and 130 K, an MAPbBr$_3$ crystal exhibited a fast and intense scintillation response, with the fast ($\tau_f$) and slow ($\tau_s$) decay components reaching 0.1 and 1 ns, respectively. The light yield of MAPbBr$_3$ was estimated to be 90000±18000 ph/MeV at 77 K and 116000±23000 ph/MeV at 8 K.

The scintillation light yield and decay time of MAPbBr$_3$ crystals were investigated over the temperature range 8-295 K. It was found that at cryogenic temperatures the perovskite crystals exhibited high light yield (>100000 ph/MeV) and sub-nanosecond decay times. This finding underpinned the potential of OTP for detector applications that rely on fast timing of scintillation detectors at cryogenic temperatures. Synchrotron radiation was used for measurements of timing characteristics and a multi-photon counting technique was used for measuring the scintillation light yield at cryogenic temperatures.

Figure 6:
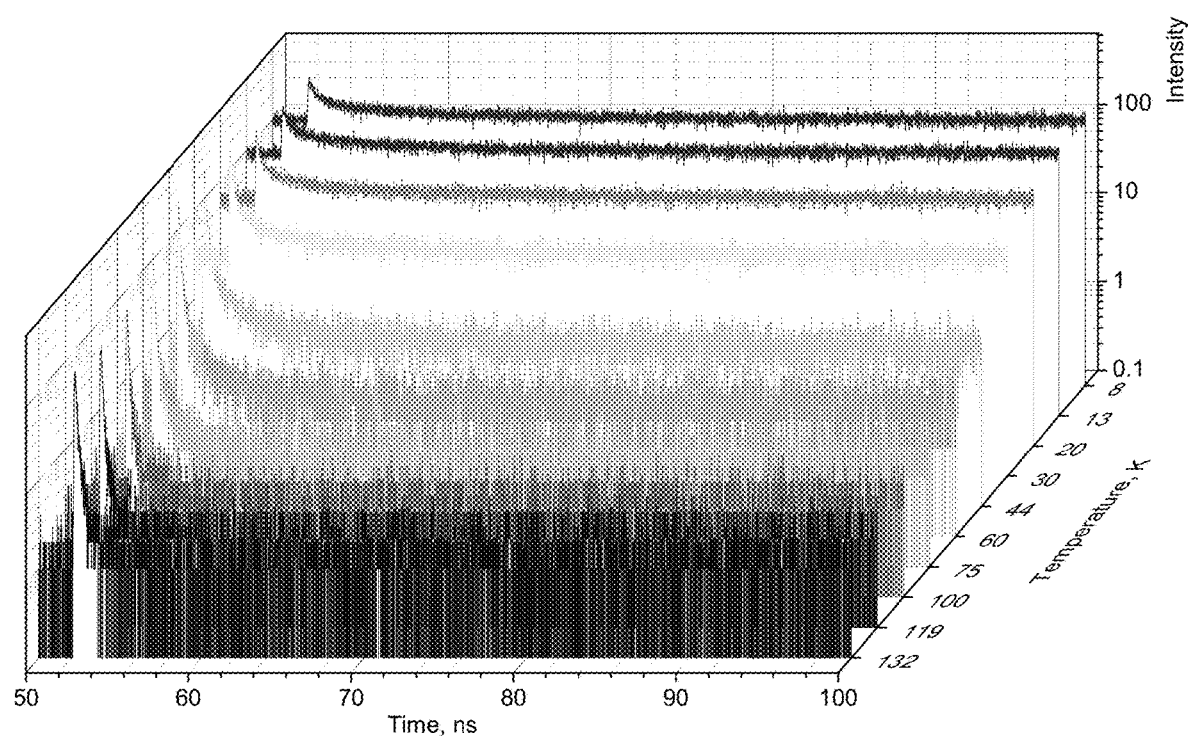
FIG. 6 is a graph that illustrates X-ray luminescence measured in illustrative perovskite scintillators at different temperatures.

Referring additionally to FIG. 6, When excited with X-rays (50 ps pulses of synchrotron radiation at E=14 keV), it was found that MAPbBr$_3$ exhibits narrow, near-edge emission bands peaking at 560 nm with a pronounced temperature dependence. Scintillation kinetics of MAPbBr$_3$ crystals were studied over a wide temperature range—from 8 to 295 K—using pulsed X-ray. It was found that scintillation decay curves exhibit fast, non-exponential kinetics—which are indicative of bimolecular recombination of charge carriers.

The main feature of the measured scintillation decay curves of the MAPbBr$_3$ crystal—and common for the majority of scintillation materials—was an increase in the decay time constant with a decrease of temperature. It was observed that cooling the MAPbBr$_3$ crystal resulted in an increase of the background. Furthermore, the amplitude of the scintillation pulse initially increased with cooling but when the temperature dropped to below 50 K it started to reduce. Inspection of the plots reveals that the scintillation pulse in MAPbBr$_3$ also undergoes significant changes in shape at low temperatures—that is, the fractional contribution of the background rapidly increases and the long component of the decay curves becomes more pronounced. These features are indicative of a slowing down in the recombination dynamics.

Figure 7A:
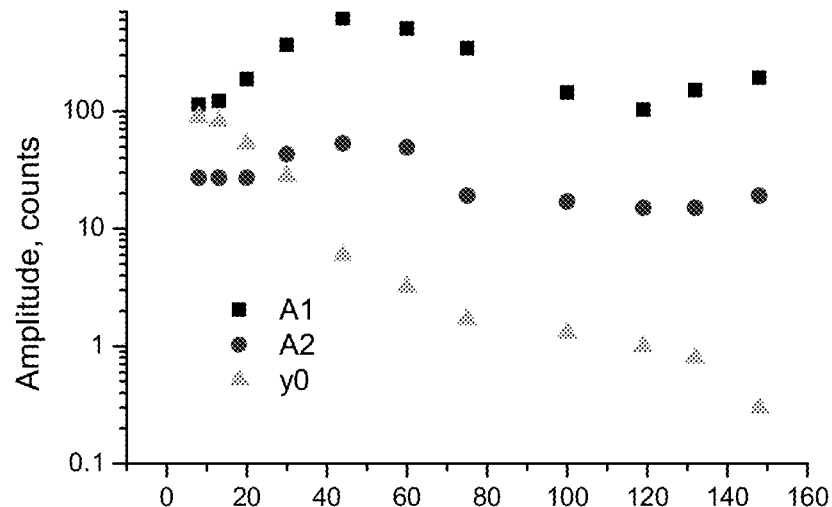
FIGS. 7A and 7B are graphs that illustrate temperature dependence of parameters of decay kinetics in illustrative perovskite scintillators.
Figure 7B:
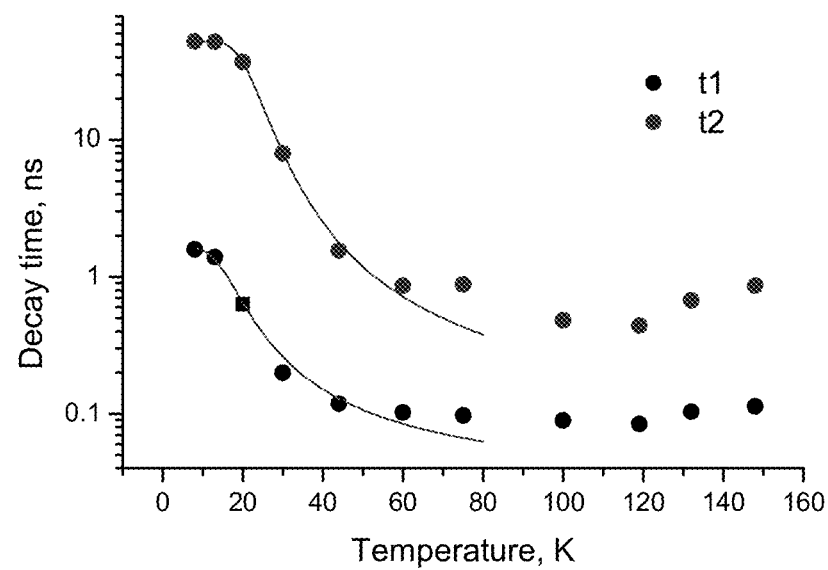

Referring additionally to FIGS. 7A and 7B, for a more quantitative comparison of these properties and trends measured decay curves were fitted with a sum of exponential functions: $f(t)=\Sigma_i A_i \exp(-t/\tau_i)+y_0$ where $A_i$ is the amplitude, $\tau_i$ the decay time constant and $y_0$ the background. As shown in FIGS. 7A and 7B, temperature dependence of decay kinetics of MAPbBr$_3$ were fitted for amplitude versus temperature (FIG. 7A) and decay time versus temperature (FIG. 7B). It will be appreciated that a best fit of $\tau=f(T)$ dependencies was found with the following parameters: $\tau_1=1.6\pm0.5$ ns; $K_1=39\pm11\times10^9$ s$^{-1}$; $\Delta E_1=6.4\pm0.5$ meV; $\tau_2=52.4\pm0.2$ ns; $K_2=18\pm3\times10^9$ s$^{-1}$; and $\Delta E_2=13.3\pm0.3$ meV. The quality of the fit was only marginally different between two- and three-exponential fits. Two exponentials and constant background were sufficient for an adequate representation of the measured decay curves.

An analysis of the plots reveals further details in the temperature evolution of the luminescence kinetics of the crystal. As can be derived from the decay time versus temperature dependences, the fast and slow decay time constants in the crystal are about 0.1 and 1 ns at T>50 K. This correlates well with the results from photoluminescence decay studies of MAPbBr$_3$ down to 77 K. With cooling to lower temperatures, the decay rate of the luminescence kinetics in MAPbBr$_3$ exhibits steep changes, thereby resulting in a significant increase of the decay time constants, so that at T=8 K, $\tau_f=2$ ns and $\tau_s=50$ ns. The amplitudes of the fast and slow components initially increase with cooling while below 40 K they start to reduce. In particular the amplitude of the fast component drops by about a factor of five. At the same time, the amplitude of the background $y_0$ exhibits a steady rise with cooling, thereby becoming comparable to the amplitude of the fast component at T=8 K. This shows that at this temperature the radiative dynamics are dominated by the slow recombination processes due to trapping and release of charge carriers. This effect causes afterglow, which has a detrimental impact upon the temporal response of the scintillator.

Importantly at T>60 K the fast and slow scintillation components dominate in the radiative decay while the fractional contribution of the background does not exceed 1%. This implies that at the higher temperature the major fraction of the scintillation response from the crystal is released over a nanosecond time interval (following an excitation pulse). This is further supported through the measurements of the scintillation light yield discussed later.

Scintillation response of MAPbBr$_3$ is shown in FIG. 8A by comparing its scintillation response with that of an LYSO—Ce scintillator. Normalized scintillation decay curves were observed at excitation by 14 keV X-ray pulses in MAPbBr$_3$ (T=77 K, curve 54) in comparison with LYSO—Ce (T=292 K, curve 56). Another example is given in FIGS. 8B and 8C—which display the sequence of X-ray pulses from the synchrotron (FWHM=60 ps, interval 11 t=2 ns) as detected by MAPbBr$_3$ and LYSO—Ce. Normalized scintillation decay curves observed at excitation by 14 keV X-ray pulses in MAPbBr$_3$ (T=77 K-curve 58) in comparison with LYSO—Ce (T=292 K, curve 60). It is clear from FIGS. 8A and 8B that the timing performance of the MAPbBr$_3$ crystal, exhibiting sub-nanosecond decay time, may be superior in comparison with LYSO—Ce. The latter exhibits a decay time constant of 33 ns and offers an example of one of the best results in coincidence timing resolution which relies on fast timing.

Numerous studies for the luminescence properties of MAPbX$_3$, X=Br and I, were conducted over a wide temperature range evidencing that free charge carriers dominate at room temperature while excitons are stable at low temperature. At high-energy excitation, the thermalized electrons and holes form free excitons which in turn can interact with defects or impurities. The narrow luminescence bands with a small Stokes shift observed in OTPs at low temperature are attributed to free and bound excitons. The luminescence is very bright at low temperature but exhibits significant thermal quenching. This is due to the exciton binding energies being tens of meV and the increase in temperature causing dissociation. Yet other characteristic features of exciton emission are the fast decay kinetics. The free excitons emit promptly while the excitations captured at defect or impurity sites recombine more slowly through de-trapping. Consequently, the scintillation mechanism in the crystals at low temperatures is controlled by two main processes that give rise to the fast and slow emission component. The fast decay component correspond to the radiative decay of free excitons while the slow component of the emission is attributed to the radiative decay of electron and holes released from the traps.

The observed temperature dependence of the luminescence decay in both channels can be explained in the framework of a simple quantitative model by considering the dynamics of radiative and non-radiative transitions between the excited and ground states of the emission center. In terms of this model the measured transition rate (the inverse of the luminescence decay constant τ) can be determined as the sum of the radiative ($k_r$) and non-radiative ($k_{nr}$) rates:

$$\frac{1}{\tau} = k_r + k_{nr} = \frac{1}{\tau_r} + \frac{1}{\tau_{nr}}, \tag{1}$$

The changes in decay time with temperature are attributed to the process of depopulation of excited state through the thermally promoted transfer of excited particles over the energy barrier that leads to the non-radiative decay. The rate associated with the non-radiative process exhibits a strong temperature dependence, thus controlling the variation of the non-radiative decay with temperature:

$$\frac{1}{\tau_{nr}} = K \exp\left(\frac{-\Delta E}{kT}\right), \tag{2}$$

where K is the probability of non-radiative decay, ΔE is the activation energy for the nonradiative transitions, and k is the Boltzmann constant. Substituting (2) into (1) brings about the classical formula:

$$\frac{1}{\tau} = \frac{1}{\tau_r} + K \exp\left(\frac{-\Delta E}{kT}\right), \tag{3}$$

Using this formula, experimental results (see FIGS. 7A and 7B) were fitted and were found to successfully describe the τ=$f$(T) dependence over a range of low temperatures from 8 to 80 K. This dependence indicates that at these temperatures the radiative decay of free and bound excitons is controlled by the thermal activation processes. However, at higher temperature there is a disparity between the model and experimental results evidencing that the model based on the assumption of isolated emission channel is not valid anymore. It is posited that this disparity is rather an expected observation that can be explained as following: at higher temperature, when the excitons start to dissociate and an electron-hole pair can escape trapping sites without recombination, there is a probability for particles to exchange between different radiative decay channels. In other words, the recombination of free and bound excitons may contribute to both emission components of luminescence decay. This effect manifests itself by an increase of the decay time constant with heating which is also observed at photoexcitation. It is worth pointing out that OPT crystals possess exceptionally low trap densities. Consequently, radiative decay is a dominant channel for the relaxation of excited states. This is one main cause for the very high luminosity at low temperatures when thermal quenching is suppressed.

Figures 9A, 9B:
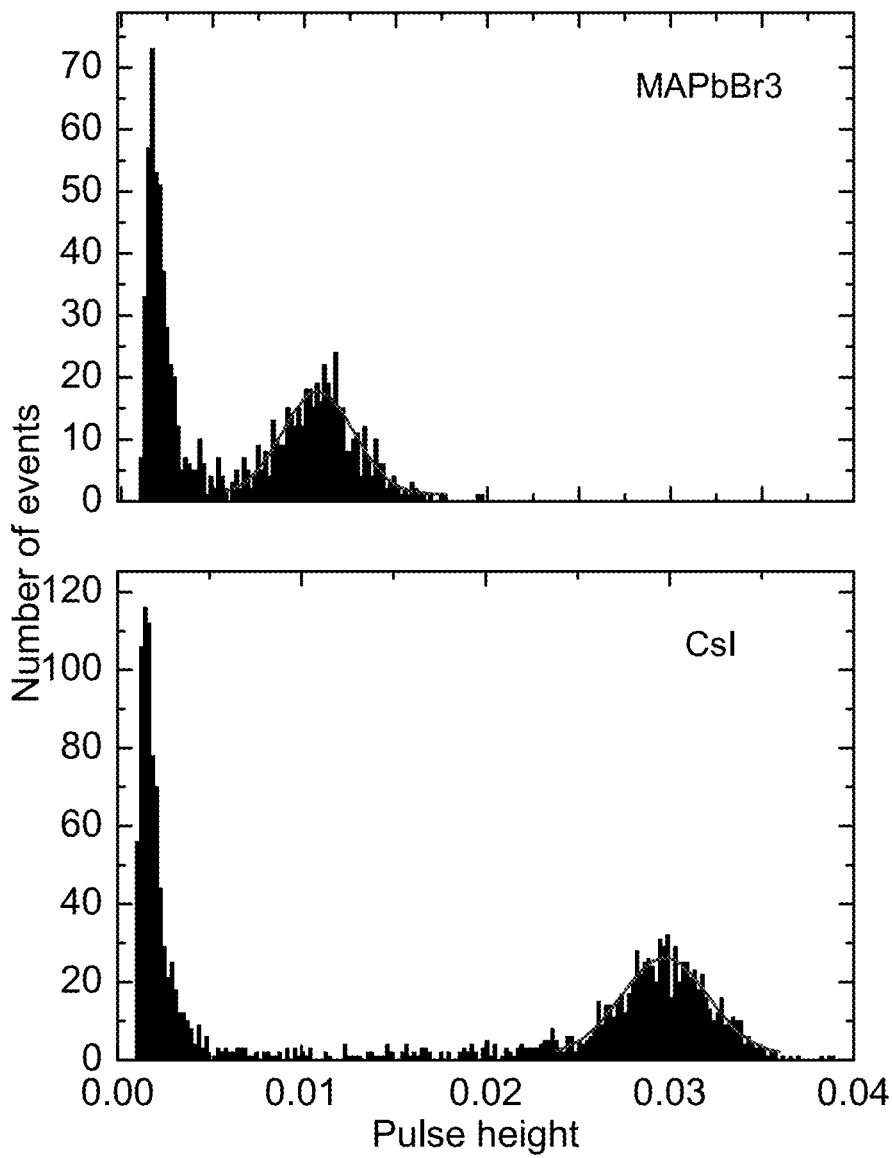
FIG. 9A is a graph of pulse height of spectra of scintillations in a perovskite scintillator.
FIG. 9B is a graph of pulse height of spectra of scintillations in a CsI scintillator.

Further to assess the performance of MAPbBr$_3$ as a scintillator, a series of energy spectra induced by a-particles in MAPbBr$_3$ were studied as a function of temperature. FIGS. 9A and 9B show pulse height spectrum measured at 50 K that feature a peak with Gaussian shape attributed to the detection of 5.5 MeV a-particles emitted by an 241 Am source by an MAPbBr$_3$ crystal at 50 K (FIG. 9A) and a CsI crystal at 50 K (FIG. 9B). Pulse height spectra distributions of scintillations excited through a-particle interaction from 241 Am in MAPbBr$_3$ at 50 K and CsI at 50 K before correction for the spectral response of the photomultiplier signify scintillation response due to a-particles that are fitted by Gaussians.

Figure 10:
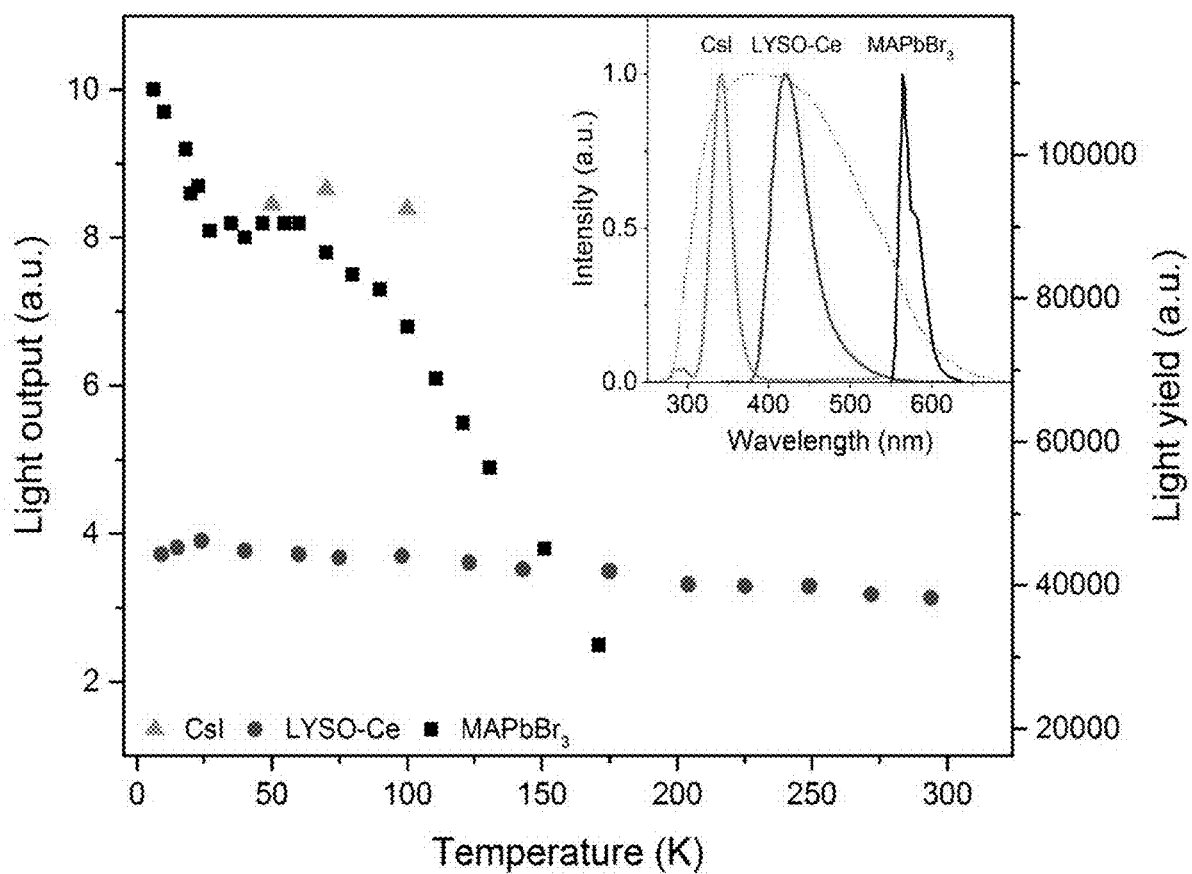
FIG. 10 is a graph of scintillation light yield as a function of temperature for various crystals.

It will be appreciated that position of the peak center is proportional to the amplitude of the scintillation response of the crystal so that it can be used as a measure of scintillation light output at different temperatures. As shown in FIG. 10, variation of the scintillation light output of the MAPbBr$_3$ crystal is shown with temperature (together with CsI and LYSO—Ce). A clearly measurable scintillation response can be detected when the crystal is cooled to below 180 K. The scintillation efficiency of MAPbBr$_3$ increases gradually as the temperature is decreased until a plateau is reached at around 70 K. At T>60 K the individual scintillation event recorded by the data acquisition system exhibits a very short, intense peak that decays within a hundred nanoseconds. This peak is caused by the overlap of many scintillation photons arriving over a short time initial interval after excitation by an alpha particle. Hence, at these temperatures only the fast emission contributes to the scintillation signal. An increase of the light output by about 20% is observed as the temperature decreases to below 30 K. This rise correlates with the rapid increase of the fractional contribution of the afterglow observed at very low temperatures.

It was also noted that as the temperature reduces to below 50 K, a delayed signal appears and is distributed over the entire time window of the 1.6 ms used to record the individual scintillation events. This delayed signal is responsible for the additional emission enhancement observed over this temperature range. It is due to the process of radiative recombination of charge released by shallow traps with activation energies between 10 and 90 meV as established from thermoluminescence data.

Having demonstrated that over the 50-150 K temperature range $MAPbBr_3$ crystals exhibit fast scintillations, and taking into consideration the theoretical estimates, the scintillation light yield was evaluated using as reference commercial CsI scintillators and LYSO—Ce scintillators. As is known, in such evaluations it is preferable to use a reference scintillator with characteristics not too dissimilar to the crystals under study. Undoped CsI has a very high light output of ~100000 ph/MeV at 77 K and exhibits strong temperature dependence, although the decay time is relatively long (~1 μs at 77 K). LYSO—Ce is known for its high light yield (34000 ph/MeV) and fast decay time—both changing only insignificantly with cooling. The light collection efficiency of the experimental setup used in this study was determined predominantly by the geometrical factors that are constant parameters. Because of low penetration depth, the energy of alpha particles is fully absorbed by the thin samples, hence the scintillation light yield could be evaluated by comparing the measured light outputs of the reference scintillator and the perovskite crystals corrected for the difference in the emission-weighted spectral sensitivity $\varepsilon_{80}$.

Referring now to FIG. 10, light output of scintillators is plotted as a function of temperature. The emission spectra of $MAPbBr_3$, CsI and LYSO—Ce crystals are shown in FIG. 10 and the quantum sensitivity of the photomultiplier used for the calculation of the emission-weighted sensitivity $\varepsilon_\lambda$ is shown in the inset of FIG. 10. Scintillation light yield as function of temperature for the $MAPbBr_3$ crystal (squares) was measured for excitation with 5.5 MeV alpha particles from 241 Am. The plot also displays the comparison with measurements of commercial CsI scintillators (triangles) and LYSO—Ce scintillators (circles) with known light yield. The inset shows normalized emission spectra of CsI (T=77 K), LYSO—Ce (T=295 K), and $MAPbBr_3$ (T=10 K). The dotted line is the normalized quantum sensitivity of the photomultiplier 9124A used in the measurements of the scintillation light yield.

Taking the light yield of CsI equal to 100000 ph/MeV at 77 K, it was determined that the light yield of $MAPbBr_3$ is equal to 90000 ph/MeV at 77 K and 116000 ph/MeV at T=8 K. On the other hand, measuring LYSO—Ce, it was found that the scintillation light yield increases to 40500 ph/MeV upon cooling to T=8 K, thereby giving a light yield of $MAPbBr_3$ equal to 110000 ph/MeV at this temperature. The estimated values correlate very well despite the relatively large error ±20%, which stems from the uncertainty of $\varepsilon_\lambda$ and the determination of the centroid in the pulse height spectra. The significance of these values can be appreciated in full when compared with the characteristics of the best modern scintillators (see Table 1).

TABLE 1

I Properties of modern scintillation materials at room temperature. Data for CsI and $MAPbBr_3$ are shown at T = 77 K.

| Crystal | Density, g/cm$^3$ | Photoelect. absorption at 511 keV, cm$^{-1}$ * | Emission peak, nm | Decay time, ns | Light yield, ph/MeV | Light yield/ decay time, ns$^{-1}$ |
|---|---|---|---|---|---|---|
| CsI—Tl | 4.5 | 0.09 | 560 | 1000 | 57000 | 57 |
| SrI$_2$—Eu | 4.6 | 0.07 | 435 | 1200 | 120000 | 100 |
| CsI (77 K) | 4.5 | 0.09 | 340 | 730/3200 | 100000 | 163 |
| LYSO-Ce | 7.1 | 0.25 | 420 | 33 | 34000 | 940 |
| GGAG-Ce | 6.2 | 0.12 | 540 | 32/156 | 45000 | 1400 |
| BaF$_2$ | 4.9 | 0.08 | 220/310 | 0.8/630 | 1800/10000 | 2250 |
| LuI$_3$—Ce | 5.6 | 0.16 | 475; 520 | 31/140/1000 | 98000 | 3160 |
| LaBr$_3$—Ce | 5.0 | 0.05 | 355; 390 | 16 | 74000 | 4630 |
| MAPbBr$_3$ (77 K) | 3.6 | 0.13 | 560 | 0.1/1 | 90000 | 90000 |

* caculated using XCOM web-tool

Figure 11:
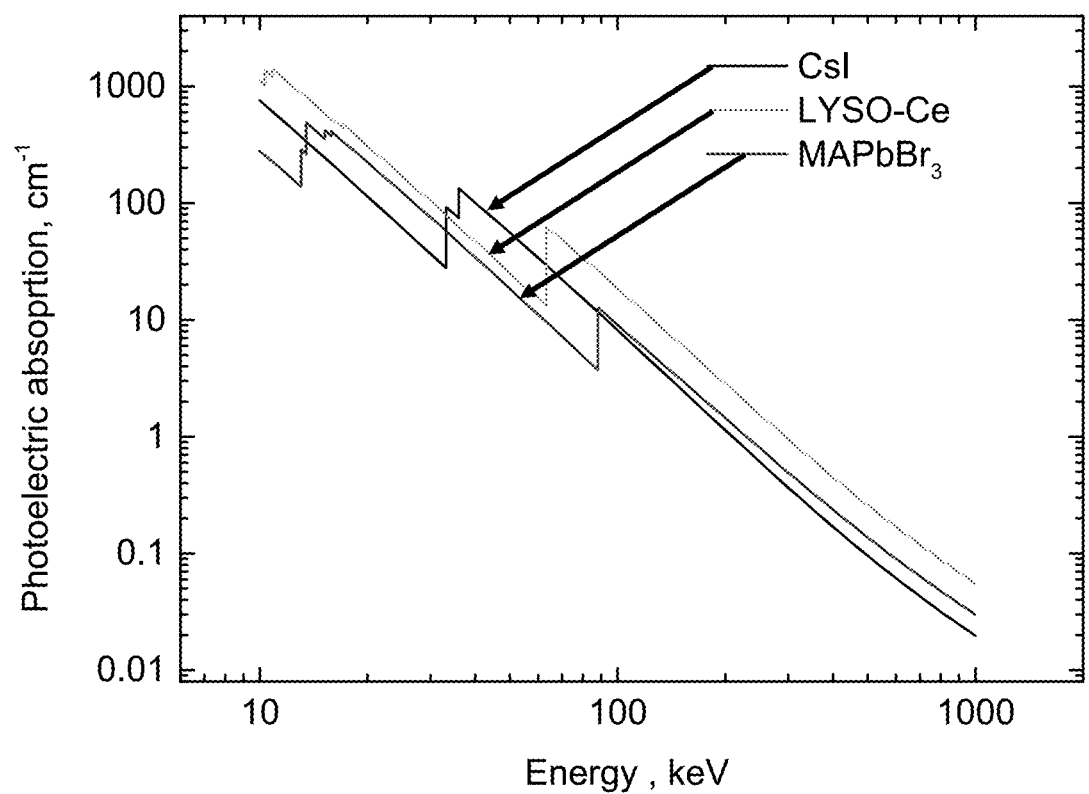
FIG. 11 is a graph of photoelectric absorption of gamma rays in CsI scintillators, LYSOCe scintillators, and perovskite scintillators.

A comparison of the $MAPbBr_3$ parameters with commercial scintillators shows that OTPs are very promising scintillation materials. Of particular note is the high initial photon density calculated as the ratio of light yield to decay time—the most important parameter that determines the timing precision of the scintillator detector. The higher density of photons near the peak enables a higher precision in determining the time of interaction. A conservative evaluation shows that this parameter is higher by a factor 20 in $MAPbBr_3$ compared to the best modern scintillator LaBr$_3$—Ce. It should be noted that there are a few other materials with fast scintillations at cryogenic temperatures discussed in literature (ZnO, PbI$_2$, HgI$_2$) but a low value of the light yield is a major limitation. The stopping power of $MAPbBr_3$ that is defined by the photoelectric fraction of the absorption coefficient is also very competitive in comparison with other scintillators; only two materials exhibit a higher value. Referring additionally to FIG. 11, the energy dependence of the photoelectric absorption of gamma rays in CsI, LYSO—Ce, and $MAPbBr_3$ is shown. The data were calculated using XCOM web-tool.

In summary, the decay time and light output of $MAPbBr_3$ crystals were measured down to a temperature of 8 K, using X-ray and particle excitation. Fast and intense scintillation response—the key characteristics for a scintillation detector—were found. At 77 K the fast and slow components of the decay were found to be ~0.1 ns and 1 ns, respectively. The light yield of $MAPbBr_3$ was estimated as 90000±18000 ph/MeV at 77 K and 116000±23000 ph/MeV at 8 K. It will be appreciated that the advanced scintillation characteristics of OTP crystals were attained even at moderate cooling to a temperature just below 100 K—which can be achieved easily through liquid nitrogen-based refrigeration systems. Modem developments in cryogenics made these temperatures also accessible though using dry cryogenic systems while advances in CMOS silicon photodetectors allow reliable detection of single photons at these temperatures.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus, comprising:
a perovskite scintillator configured to be irradiated by ionizing radiation at a selected operating temperature that is below 120 K and above 20 K, where the selected operating temperature is selected based, at least in part, on a material of the perovskite scintillator to yield a light output with:
(i) a decay time constant that decreases as the temperature decreases within the selected operating temperature range,
(ii) a maximum fast component amplitude, A1, that is at least two times greater than a maximum slow component amplitude, A2,
(iii) an afterglow, y0, that is at least two times less than the amplitude of the maximum slow component amplitude, A2, and
(iv) a fast decay time constant, t1, and a slow decay time constant, t2, that are each less than 10 nanoseconds.

2. The apparatus of claim 1, wherein the perovskite scintillator includes an organic-inorganic trihalide perovskite ("OTP") scintillator.

3. The apparatus of claim 1, wherein a timing resolution of the perovskite scintillator is less than 200 ps.

4. The apparatus of claim 1, wherein a light yield of the perovskite scintillator is at least 50000 ph/MeV.

5. The apparatus of claim 1, further comprising:
a cooling system configured to cool the perovskite scintillator to the operating temperature.

6. The apparatus of claim 1, wherein the operating temperature is about 77 K.

7. The apparatus of claim 1, further comprising:
encapsulation material in which the perovskite scintillator is encapsulated.

8. The apparatus of claim 1, wherein a scintillation light yield to decay time ratio of the perovskite scintillator in response to the ionizing radiation is greater than 8000 ns$^{-1}$ at the operating temperature.

9. A detector comprising:
a source of ionizing radiation;
at least one perovskite scintillator configured to be irradiated by ionizing radiation at a first frequency from the source of ionizing radiation and emit photons responsive thereto at a second frequency that is lower than the first frequency, the perovskite scintillator configured to be operated at a selected operating temperature below 120 K and above 20 K;
a cooling system configured to cool the perovskite scintillator to the operating temperature; and
a photodetector configured to detect photons emitted by the perovskite scintillator,
wherein the perovskite scintillator, operated at the selected operating temperature, is configured to yield a light output in response to irradiation by the ionizing radiation that has:
(i) a decay time constant that decreases as the temperature decreases within the selected operating temperature,
(ii) a maximum fast component amplitude, A1, that is at least two times greater than a maximum slow component amplitude, A2,
(iii) an afterglow, y0, that is at least two times less than the amplitude of the maximum slow component amplitude, A2, and
(iv) a fast decay time constant, t1, and a slow decay time constant, t2, that are each less than 10 nanoseconds.

10. The detector of claim 9, wherein a scintillation light yield to fast decay time ratio of the perovskite scintillator in response to irradiation by the ionizing radiation is greater than 8000 ns$^{-1}$ at the operating temperature.

11. The detector of claim 9, wherein the source of ionizing radiation includes a source chosen from a group comprising an X-ray source and a gamma ray source.

12. A scanner comprising:
a perovskite scintillator to be irradiated by pairs of ionizing gamma photons at a first frequency and emit photons responsive thereto at a second frequency that is lower than the first frequency, the perovskite scintillator configured to be operated at a selected operating temperature between 120 K and 20 K;
a cooling system configured to cool the perovskite scintillator to the selected operating temperature; and
a photodetector configured to detect photons emitted by the perovskite scintillator,
wherein the perovskite scintillator, operated at the selected operating temperature, is configured to yield a light output in response to irradiation by the ionizing radiation that has:
(i) a decay time constant that decreases as the temperature decreases within the selected operating temperature,
(ii) a maximum fast component amplitude, A1, that is at least two times greater than a maximum slow component amplitude, A2,
(iii) an afterglow, y0, that is at least two times less than the amplitude of the maximum slow component amplitude, A2, and
(iv) a fast decay time constant, t1, and a slow decay time constant, t2, that are each less than 10 nanoseconds.

13. The scanner of claim 12, wherein the photodetector is configured to be cooled to a cooled temperature.

14. The scanner of claim 13, wherein the cooled temperature is different from the operating temperature.

15. The scanner of claim 13, wherein the cooled temperature is higher than the operating temperature.

16. The scanner of claim 12, wherein the photodetector has a coincidence resolving time of less than 1,000 ps.

17. The scanner of claim 16, wherein the photodetector has a coincidence resolving time of less than 10 ps.

18. The scanner of claim 12, further comprising at least one non-perovskite scintillator disposed adjacent the perovskite scintillator, wherein the non-perovskite scintillator is configured to be irradiated by ionizing radiation at a third frequency from the source of ionizing radiation and emit photons responsive thereto at a fourth frequency that is lower than the third frequency, the photodetector being further configured to detect photons emitted by the non-perovskite scintillator.

19. The scanner of claim 18, wherein the non-perovskite scintillator includes a high atomic number scintillator.

20. The scanner of claim 18, wherein the first frequency and the third frequency are the same.

21. The scanner of claim 12, further comprising:
a plurality of perovskite scintillators; and
a plurality of non-perovskite scintillators,
wherein single ones of the plurality of perovskite scintillators are disposed adjacent single ones of the plurality of non-perovskite scintillators.

22. The scanner of claim 12, wherein the scanner includes a tomography scanner.

* * * * *